(12) United States Patent
Boudjelal et al.

(10) Patent No.: US 10,253,371 B2
(45) Date of Patent: Apr. 9, 2019

(54) METHOD OF TREATING LEUKEMIA BASED ON GENE EXPRESSION OF CLOCK GENES

(71) Applicants: National Guard Health Affairs, Riyadh (SA); King Saud bin Abdulaziz University for Health Sciences, Riyadh (SA); King Abdullah International Medical Research Center, Riyadh (SA)

(72) Inventors: Mohamed Boudjelal, Riyadh (SA); Ahmed Al Askar, Riyadh (SA); Alshaimaa Alhallaj, Riyadh (SA); Atef Nehdi, Riyadh (SA); Hina Rehan, Riyadh (SA); Sabhi Rahman, Riyadh (SA); Gamal Edin Gmati, Riyadh (SA); Khadega A. Abuelgasim, Riyadh (SA)

(73) Assignees: National Guard Health Affairs, Riyadh (SA); King Saud bin Abdulaziz University for Health Sciences, Riyadh (SA); King Abdullah International Medical Research Center, Riyadh (SA)

( * ) Notice: Subject to any disclaimer, the term of this patent is extended or adjusted under 35 U.S.C. 154(b) by 23 days.

(21) Appl. No.: 15/249,863

(22) Filed: Aug. 29, 2016

(65) Prior Publication Data

US 2018/0057886 A1    Mar. 1, 2018

(51) Int. Cl.
| | | |
|---|---|---|
| C12Q 1/68 | (2018.01) | |
| G01N 33/53 | (2006.01) | |
| C12Q 1/6886 | (2018.01) | |
| A61K 31/506 | (2006.01) | |
| A61K 31/498 | (2006.01) | |
| A61K 31/5025 | (2006.01) | |
| A61K 31/255 | (2006.01) | |
| A61K 31/675 | (2006.01) | |
| A61K 31/7068 | (2006.01) | |

(52) U.S. Cl.
CPC .......... *C12Q 1/6886* (2013.01); *A61K 31/255* (2013.01); *A61K 31/498* (2013.01); *A61K 31/506* (2013.01); *A61K 31/5025* (2013.01); *A61K 31/675* (2013.01); *A61K 31/7068* (2013.01); *C12Q 2600/106* (2013.01); *C12Q 2600/158* (2013.01)

(58) Field of Classification Search
None
See application file for complete search history.

(56) References Cited

U.S. PATENT DOCUMENTS

| 9,141,756 B1 | 9/2015 | Hillis et al. | |
|---|---|---|---|
| 2009/0202659 A1* | 8/2009 | Gimble | A61K 31/4015 424/663 |
| 2011/0059852 A1* | 3/2011 | Karsunky | C07K 16/28 506/7 |
| 2012/0072124 A1* | 3/2012 | Radich | C12Q 1/6886 702/20 |
| 2015/0299803 A1* | 10/2015 | Rodrigueza | C12Q 1/6886 424/9.2 |
| 2016/0298195 A1* | 10/2016 | Armstrong | C12Q 1/6886 |

FOREIGN PATENT DOCUMENTS

| WO | WO 03/025151 A2 | 3/2003 |
|---|---|---|
| WO | WO 2009/013614 A2 | 1/2009 |
| WO | WO 2015/160986 A2 | 10/2015 |

OTHER PUBLICATIONS

Liu et al Clinical Immunology. 2004. 112: 225-230.*
Coleman, R. Drug Discovery Today. 2003. 8: 233-235.*
Ming-Yu Yang, et al., "Altered Expression of Circadian Clock Genes in Human Chronic Myeloid Leukemia", Journal of Biological Rhythms, vol. 26, No. 2, Apr. 2011, pp. 136-148.
Sigal Gery, et al., "Per2 Is a C/EBP Target Gene Implicated in Myeloid Leukemia", Integrative Cancer Therapies, vol. 8, No. 4, 2009, pp. 317-320.
Ming-Luen Hu, et al., "Deregulated expression of circadian clock genes in gastric cancer", Gastroenterology, vol. 14, 2014, 8 pages.
Ming-Yu Yang, et al., "Up-regulation of PER3 Expression Is Correlated with Better Clinical Outcome in Acute Leukemia", Anticancer Research, vol. 35, No. 12, Dec. 2015, pp. 6615-6622 (Abstract only).
Sobia Rana, et al., "Deregulated expression of circadian clock and clock-controlled cell cycle genes in chronic lymphocytic leukemia", Molecular Biology Reports, vol. 41, Issue 1, Jan. 2014, pp. 95-103 (Abstract only).
Maher Hanoun, et al., "Epigenetic Silencing of the Circadian Clock Gene CRY1 is Associated with an Indolent Clinical Course in Chronic Lymphocytic Leukemia", PLOS One, vol. 7, No. 3, Mar. 28, 2012, 13 pages.
Takao Miki, et al., "PML regulates PER2 nuclear localization and circadian function", the EMBO Journal, vol. 31, No. 6, Mar. 21, 2012, pp. 1427-1439.
Hiroaki Taniguchi, et al., "Epigenetic Inactivation of the Circadian Clock Gene *BMAL1* in Hematologic Malignancies", Cancer Research Molecular Biology, Pathobiology, and Genetics, vol. 69, No. 21, Nov. 1, 2009, 18 pages.
Ming-Yu Yang, et al., "Downregulation of circadian clock genes in chronic myeloid leukemia: Alternative methylation pattern of *hPER3*", Cancer Science, vol. 97, Issue 12, Dec. 2006, pp. 1298-1307 (Abstract only).
Sigal Gery, et al., "Transcription profiling of C/EBP targets identifies *Per2* as a gene implicated in myeloid leukemia", Blood, vol. 106, No. 8, Oct. 15, 2005, pp. 2827-2836.

* cited by examiner

*Primary Examiner* — Carla J Myers
(74) *Attorney, Agent, or Firm* — Oblon, McClelland, Maier & Neustadt, L.L.P.

(57) ABSTRACT

A method of treating leukemia in a patient, the method including obtaining a plasma sample from a patient at a first time point and at a second time point, measuring a gene expression level of a set of core clock genes, and at least one of a first set of peripheral clock genes and a second set of peripheral clock genes, each in the plasma sample at the first time point and in the plasma sample at the second time point. Then determining that a first treatment is effective or ineffective for the patient when a correlation of the gene expression level of the set of core clock genes, the first set of peripheral clock genes, and the second set of peripheral clock genes, and treating the patient accordingly.

13 Claims, 12 Drawing Sheets

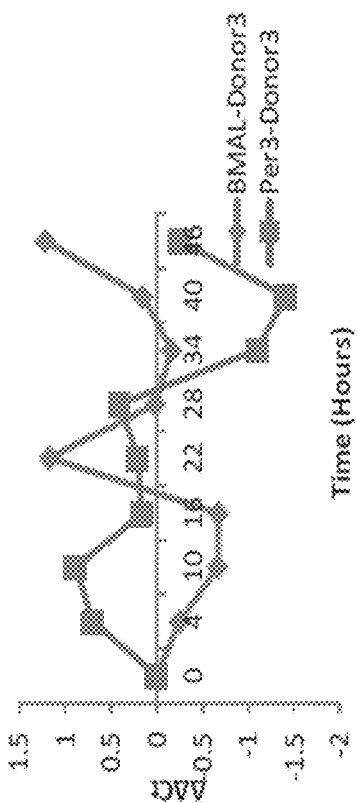
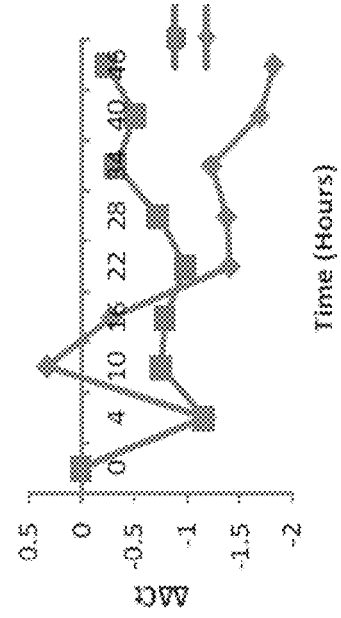
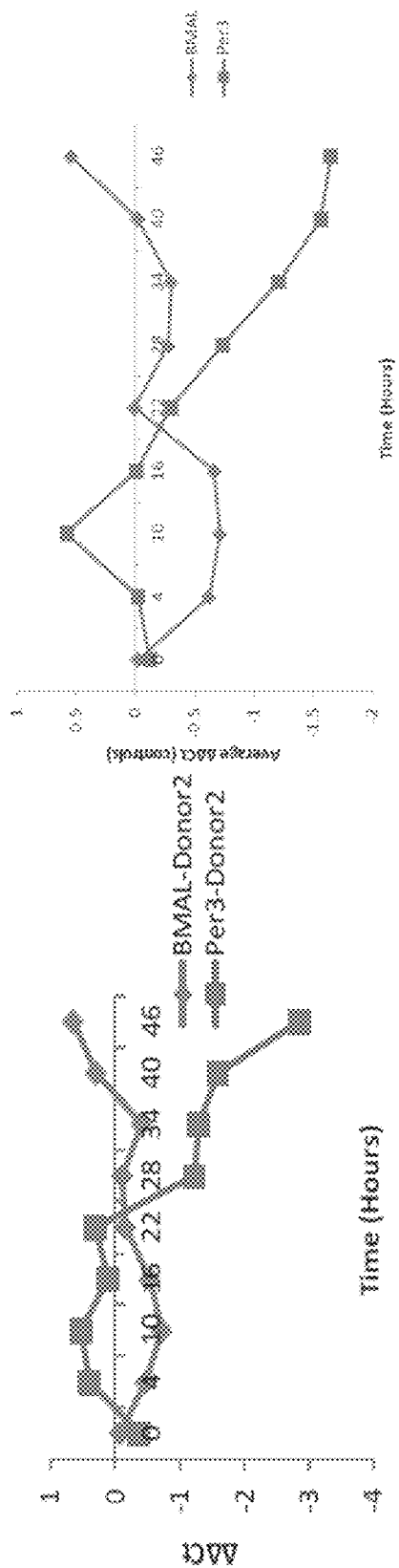
Fig. 9A
Fig. 9B
Fig. 9C
Fig. 9D

Patient 3

Patient 3
Diagnosis: AML
Gender: Female
Age: 73 years old

Patient 4

Patient 4
Diagnosis: AML
Gender: Male
Age: 63 years old

METHOD OF TREATING LEUKEMIA BASED ON GENE EXPRESSION OF CLOCK GENES

BACKGROUND OF THE INVENTION

Technical Field

The present disclosure relates to a method for administering a subsequent course of a treatment to a subject having myelogenous leukemia based on an effectiveness of a present course of treatment evaluated by gene expression levels in core clock genes and peripheral clock genes.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present disclosure.

The regulation of the body rhythm is directed by the biological clock, which is commonly referred to as the circadian rhythm. The biological clock maintains the body's adaptation to environmental changes during the day and night through regulating the pathways governing many physiological processes. The biological clock exists in both prokaryotic and eukaryotic organisms. It is an important component of the cells and organs. Two clock systems exist in the mammalian system. The central clock that is located in the suprachiasmatic nucleus (SCN), which can synchronize the secondary clocks, which are found in the peripheral organs and tissues through hormonal secretion such as melatonin and cortisol as well as modulating the body temperature. See Relógio A, Westermark P O, Wallach T, Schellenberg K, Kramer A, Herzel H, (2011) Tuning the mammalian circadian clock: robust synergy of two loops. PLoS Comput Biol 7:1, incorporated herein by reference in its entirety.

The molecular clock can regulate a complex network of genes and pathways that leads to oscillations within a period of approximately 24 hours. Comprehensive studies have been performed to analyze the circadian clock in mammals in order to understand its role in health and diseases. These studies found that up to 20% of the genome is directed by the circadian clock, which has many regulatory functions that are related to the cell cycle. Importantly, disruption of the clock function can damage the organism. See Loudon A S (2012) Circadian biology: a 2.5 billion year old clock. Current Biol 24:22, incorporated herein by reference in its entirety.

Anatomically, there is a complex neuronal network in the anterior hypothalamus that constitutes the SCN central pacemaker which is involved in producing synchronized outputs to regulate the clock in the brain and in the peripheral clocks in different tissues throughout the body. These later clocks are self-sustained: circadian oscillations intrinsic to each cell can occur autonomously, without any environmental signals. To sustain the oscillation of the peripheral clocks at the approximate periodicity of 24 hours, synchronization is influenced by the external signals that are known as zeitgebers. The synchronization process, also called entrainment, is an important aspect to reset the clock daily and to prevent it from running out of phase. Light is the most relevant external signal that can synchronize the central clock, it is detected by the photoreceptor cells in the retina and the signal get transmitted via the retino-hypothalamic tract (RHT) in the SCN. See Masri S, Zocchi L, Katada S, Mora E, Sassone-Corsi P (2012) The circadian clock transcriptional complex: metabolic feedback intersects with epigenetic control. Ann N Y Acad Sci 1264:103-109, incorporated herein by reference in its entirety. This in turn sets the cascade of signaling pathways to stimulate the neurons that lead to the activation of a transcriptional program of clock-controlled genes (CCGs). In the non-brain tissues, such as liver, heart, kidney and skin, the peripheral clocks are involved in the regulation of local transcriptional activity. These clocks are also entrained by external cues mainly temperature and feeding schedules. See Buhr E D, Yoo S H, Takahashi J S (2010) Temperature as a universal resetting cue for mammalian circadian oscillators. Science 330:379-385, incorporated herein by reference in its entirety.

Across species, the molecular mechanisms of the biological clock are evolutionarily conserved and its role is important for maintaining advantageous organism activity and regulation of several processes at the cellular level. It directs the sleep-awake cycles, memory consolidation, metabolism of nutrients, toxins and drugs, bone formation, hormone regulation, immunity, cell growth and cycle. Several pathways are also known to be highly regulated by the clock, such as heart rate, blood pressure and body temperature. See Chaudhury D, Wang L M, Colwell C S (2005) Circadian regulation of hippocampal long-term potentiation. J Biol Rhythms 20:225-236; Masri S, Sassone-Corsi P (2012) The circadian clock: a framework linking metabolism, epigenetics and neuronal function. Nat Rev Neurosci 14:69-75; and Levi F, Schibler U (2007) Circadian rhythms: mechanisms and therapeutic implications. Annu Rev Pharmacol Toxicol 47:593-628, each incorporated herein by reference in its entirety. In addition, many diseases and disorders are also associated with malfunctions of the circadian clock, such as cancer, familial sleep disorders (FASPS), bipolar disorder, sleep problems in the elderly, seasonal affective disorders (SAD), diabetes and obesity. See Vanselow K, Vanselow J T, Westermark P O, Reischl S, Maier B, et al. (2006) Differential effects of PER2 phosphorylation: molecular basis for the human familial advanced sleep phase syndrome (FASPS), Genes Dev 20:2660-2672; Takahashi J S, Hong H K, Ko C H, McDearmon E L (2008) The genetics of mammalian circadian order and disorder: implications for physiology and disease, Nat Rev Genet 9:764-775; Ptacek L J, Jones C R, Fu Y H (2007) Novel insights from genetic and molecular characterization of the human clock, Cold Spring Harb Symp Quant Biol 72:273-277; and Marcheva B, Ramsey K M, Buhr E D, Kobayashi Y, Su H, et al. (2007) Disruption of the clock components CLOCK and BMAL1 leads to hypoinsulinaemia and diabetes, Nature 466:627-631, each incorporated herein by reference in its entirety. Therefore, determining the key molecules involved in controlling the functions of circadian clock is important as it will lead to a better understanding of the molecular and cellular basis of human diseases; thus developing efficient therapies that can cure many diseases such as cancer.

It is well documented that sleep and activity rhythms are altered in cancer patients and worsen when anticancer drugs are administered, at their most toxic time, and the disruption accelerates the cancer growth and shortens survival in the clinic. The interaction between the clock and cancer is further complicated by gender, clock gene mutations, and treatment type used. Many epidemiologic studies linked the circadian disruption and cancer. It has been found that male shift workers have significantly high risk of prostate cancer. See Kubo T, Ozasa K, Mikami K, et al. (2006) "Prospective cohort study of the risk of prostate cancer among rotating-shift workers: findings from the Japan collaborative cohort study," Am J Epidemiol 164:549-555, incorporated herein by reference in its entirety. Two important studies have found that extended periods of rotating night work was associated with high risk of breast cancer, colorectal cancer, endometrial cancer in female nurses. See Schernhammer E S, Laden F, Speizer F E, Willett W C, Hunter D J, Kawachi I, Colditz G A (2001) "Rotating night shifts and risk of breast cancer in women participating in the nurses' health study," J Natl Cancer Inst 93:1563-1568 and Megdal S P, Kroenke C H, Laden F, Pukkala E, Schernhammer E S (2005) Night work and breast cancer risk: a systematic review and meta-analysis. Eur J Cancer 41:2023-2032, each incorporated herein by reference in its entirety. As a result, it was suggested that the shift-work, which leads to circadian disruption, is probably carcinogenic for humans. See Straif K, Baan R, Grosse Y, Secretan B, El Ghissassi F, Bouvard V, Altieri A, Benbrahim-Tallaa L, Cogliano V (2007) "Carcinogenicity of shift-work, painting, and fire-fighting," Lancet Oncol 8:1065-1066, incorporated herein by reference in its entirety.

Important circadian proteins that form complexes are CLOCK/BMAL1 and NPAS2/BMAL1. These complexes are formed by several proteins encoded by genes including the Clock gene (circadian locomotors output cycles kaput), NPAS2 gene (Neuronal PAS domain protein 2) and Bmal gene (brain and muscle aryl hydrocarbon receptor nuclear translocator like—Arntl), which represents the central node in the network and the transcription initiator of the feedback loops. NPAS2 gene is highly related in primary amino acid sequence to CLOCK. These two genes (CLOCK and NPAS2) can drive the expression of the Period1/2 and Cryptochrome1/2 genes by binding to E-box (enhancing expression) cis-elements in the promoter regions of the Period 1, 2 and 3 genes (Per1, Per2, and Per3), and Cryptochrome genes (Cry1, Cry2).

The molecular mechanism linking the perturbation of the clock and tumor growth and survival is not very well understood. It has been shown that mice deficient for Per2 are associated with increased risk of tumor development following exposure to ionizing radiation. See Xia H C, Niu Z F, Mia H, Cao S Z, Hao S C, Liu Z T, Wang F (2010) "Deregulated expression of the Per1 and Per2 in human gliomas," Can J Neurol Sci 37:365-370, incorporated herein by reference in its entirety. Over expression of Period in human cancer cell lines increased their sensitivity to DNA damage and apoptosis. In contrast, down regulation of Period was associated with resistance against ionizing radiation induced apoptosis. See Fu L, Patel M S, Bradley A, Wagner E F, Karsenty G (2005) "The molecular clock mediates leptin-regulated bone formation," Cell 122:803-815 and Gery S, Koeffler H P (2007) "The role of circadian regulation in cancer," Cold Spring Harb Symp Quant Biol 72:459-464, each incorporated herein by reference in its entirety. In murine breast cancer models, the anti-apoptotic gene Bcl2 displayed a robust circadian oscillation in normal tissues, this rhythmicity was absent in the tumor itself. See Granda T G, Liu X H, Smaaland R, Cermakian N, Filipski E, Sassone-Corsi P, Levi F (2005) "Circadian regulation of cell cycle and apoptosis proteins in mouse bone marrow and tumor," FASEB J 19:304-306, incorporated herein by reference in its entirety.

Many studies have linked the molecular clock components and the cell cycle machinery. The mammalian cell cycle is governed by a network of cyclin-dependent kinases (Cdks). Each phase of the cell cycle is controlled by a different cyclin/Cdk complex: cyclin D/CDK4-6 and cyclin E/Cdk2 control G1 phase and the G1/S transition, respectively; cyclin A/Cdk2 allows the progression of cell cycle into the S phase and DNA replication, while cyclin B/Cdk1 involved in G2/M transition. Several lines of evidences at the cellular level, whole organ and animal models showed that the cell cycle is gated by the biological clock at different levels. First, the expression of Kinase Wee1, which inhibits the kinase Cdk1 and blocks the G2/M transition, is directly regulated by BMAL. In addition c-Myc, which promotes G1 cyclin synthesis, is inhibited by BMAL1 while p21 and cyclin E is inhibited by REV-ERBα. In addition, several components of DNA damage and repair mechanisms are also under circadian rhythm, such as the nucleotide excision repair; the Tip60, a histone acetylase of chromatin, with DNA damage response and repair competency is regulated by the CLOCK/BMAL1 complex. These studies have linked directly the molecular clock to the cell cycle, chromatin remodelling and DNA repair, which can be disturbed in cancer. It also provides evidence that perturbation of the clock can be a major risk for cancer initiation and growth. See Gérard C, Goldbeter A (2012) "Entrainment of the mammalian cell cycle by the circadian clock: modeling two coupled cellular rhythms," PLoS Comput Biol 8:e1002516; Grechez-Cassiau A, Rayet B, Guillaumond F, Teboul M, Delaunay F (2008) "The circadian clock component BMAL1 is a critical regulator of p21WAF1/CIP1 expression and hepatocyte proliferation," J Biol Chem 283:4535-4542. 36. Miyamoto N, Izumi H, Noquchi T, et al. (2008) "Tip60 is regulated by circadian transcription factor clock and is involved in cisplatin resistance," J Biol Chem 283:18218-18226, each incorporated herein by reference in its entirety.

There is a second indication how malfunction of the clock can increase the risk of cancer: Through the ability of the clock to regulate the stem cells. Stem cells in their niche are composed of two populations based on the phase of the clock. Half of the population is at night phase and second half is at the day phase. The two niches either secrete TGF-β protein or Wnt protein that have opposing effects on cell division and differentiation, a mechanism that can maintain stem cells in their pluripotent state. Once the stem cells are committed to differentiation, the balance is shifted toward TGF-β pathway. Many pathways regulate the differentiation of cancer stem cells and status of cancer stem cells can also play an important role in the function of the biological clock. For example nuclear receptors, such as glucocorticoids, steroid, estrogen and others that affect the clock also play an important role in adult and cancer stem cells fate. The involvement of histone acetylation and deacytelation in the regulation of the stem cells differentiation is another level of its link to the clock. For example, Sirt1 can deacytelase the Per2 protein and destruct the clock oscillation. It also plays an important role in regulating the developmental genes during differentiation of stem cells. Sirt1 is also involved in the development of various cancers such as prostate, breast and colorectal cancers, and chemotherapeutic drug resistance of cancer cells. See Janich P, Pascual G, Merlos-Suárez A, et al. (2011) "The circadian molecular clock creates epidermal stem cell heterogeneity," Nature 480:209-214; Bellet M M, Nakahata Y, Boudjelal M, et al. (2013) "Pharmacological modulation of circadian rhythms by synthetic activators of the deacetylase SIRT1," Proc Natl Acad Sci USA. 2013 Feb. 26, 110(9):3333-3338; Olmos Y, Brosens J J, Lam E W (2010) "Interplay between SIRT proteins and tumour suppressor transcription factors in chemotherapeutic resistance of cancer," Drug Resist Updat 14:35-44; and Calvanese V, Lara E, Suárez-Álvarez B, et al. (2010)

"Sirtuin 1 regulation of developmental genes during differentiation of stem cells," Proc Natl Acad Sci USA 107:13736-13741, each incorporated herein by reference in its entirety.

Hematopoietic malignancies, including leukemia, lymphoma and myeloma, accounts for nearly 10% of cancer-related deaths worldwide. Leukemia is a cancer of the bone marrow and blood. There are four main types of leukemia including acute lymphocytic leukemia (ALL), chronic lymphocytic leukemia (CLL), acute myelogenous leukemia (AML), and chronic myelogenous leukemia (CML). Mixed lineage leukemia (MILL) means that the leukemia comes from both the myeloid and the lymphoid cell progenitors. The cause of leukemia is currently still unknown. See Zaidi S K, Trombly D J, Dowdy C R, et al. "Epigenetic mechanisms in leukemia". Adv Biol Regul. 2012; 52(3):369-376 and Robien K, Ulrich C M. "5,10-Methylenetetrahydrofolate reductase polymorphisms and leukemia risk: a HuGE minireview," Am J Epidemiol. 2003; 157(7):571-582, each incorporated herein by reference in its entirety.

The circadian oscillation of hematopoietic stem cell-derived erythroid, myeloid, and lymphoid populations were demonstrated as well as those of circulating endothelial progenitor cells. See Thomas H E, Redgrave R, Cunnington M S, Avery P, Keavney B D, Arthur B M (2008) "Circulating endothelial progenitor cells exhibit diurnal variation," Arterioscler Thromb Vasc Biol 28:e21-e22, incorporated herein by reference in its entirety. Svetvold, Laerum, and colleagues demonstrated that the circadian oscillation of hematopoietic lineages was age dependent in such the clock displayed a good rhythmicity in young mice but its amplitude and peak decline by age. See Sletvold O, Laerum O D (1988) "Alterations of cell cycle distribution in the bone marrow of aging mice measured by flow cytometry," Exp Gerontol 23:43-58, incorporated herein by reference in its entirety. A similar profile has been reported in peripheral blood leukocytes. See Fukuya H, Emoto N, Nonaka H, Yagita K, Okamura H, Yokoyama M (2007) "Circadian expression of clock genes in human peripheral leukocytes," Biochem Biophys Res Commun 354:924-928, incorporated herein by reference in its entirety. Consistent with these observations, circulating levels of hematopoietic growth factors such as Granulocyte-Colony Stimulating Factor, Granulocyte-Monocyte Colony Stimulating Factor, Tumor Necrosis Factor, and Interleukins 2, 6, and 10 were also observed to display circadian oscillations. See Abdelaal M A, Hashim I A, Zawawi T H, Felimban S K, Sobhi E M, Jeje O, Oni G A (2000) "Circadian rhythm of granulocyte-macrophage colony-stimulating factor in normal subjects and neutropenic hospitalised patients." Ir J Med Sci 169: 55-57; Dincol D, Akbulut H, Buyukcelik A, Icli F (2000) Diurnal variations of serum GM-CSF levels. Cytokine 12:1151-1155; Sothern R B, Roitman-Johnson B, Kanabrocki E L, Yager J G, Roodell M M, Weatherbee J A, Young M R, Nenchausky B M, Scheving L E (1995) "Circadian characteristics of circulating interleukin-6 in men," J Allergy Clin Immunol 95:1029-1035; and Young M R, Matthews J P, Kanabrocki E L, Sothern R B, Roitman-Johnson B, Scheving L E (1995) "Circadian rhythmometry of serum interleukin-2, interleukin-10, tumor necrosis factor-alpha, and granulocyte-macrophage colony-stimulating factor in men," Chronobiol Int 12:19-27, each incorporated herein by reference in its entirety. In addition it has been suggested that the expression of stromal derived factor 1 (SDF1 or CXC12) is regulated by a signal from the suprachiasmatic nucleus, it is likely that the expression profile of multiple growth factors, receptors, and related metabolic enzymes will exhibit circadian characteristics. See Ptitysn A Z S, Conrad S A, Scott L K, Mynatt M L, Gimble J M (2006) "Circadian Clocks are Resounding in Peripheral Tissues," PLoS Computational Biology 2:e16 and Zvonic S, Ptitsyn A A, Conrad S A, Scott L K, Floyd Z E, Kilroy G, Wu X, Goh B C, Mynatt R L, Gimble J M (2006) "Characterization of peripheral circadian clocks in adipose tissues," Diabetes 55:962-970, incorporated herein by reference in its entirety. The circadian rhythmicity controls the cell cycle and apoptotic pathways in hematopoietic cells and the disruption of the biological clock has been implicated in hematopoietic neoplasm. See Mendez-Ferrer S., Lucas D, Battista M., Frenette P S (2008) "Haematopoietic stem cell release is regulated by circadian oscillations," Nature 452: 442-447, incorporated herein by reference in its entirety. The Per2 deficient mice are proven to have 10 fold increase of incidence of lymphomas when exposed to radiation. Moreover, the cell cycle genes, such as cyclin D1 and A, c-Myc, Mdm2 and Gadd45a is deregulated in Per2 mutant mice. See Fu L, Pelicano H, Liu J, Huang P, Lee C (2002) "The circadian gene period2 plays an important role in tumor suppression and DNA damage response in vivo," Cell 111: 41-50, incorporated herein by reference in its entirety. In addition, the forced expression of Per1 and Per2 in breast and prostate cancer cells inhibits their proliferation in culture, and inhibition of Per1 and Per2 by siRNA accelerates their proliferation. See Yang X, Wood P A, Oh E Y, Du-Quiton J, Ansell C M, Hrushesky W J (2009) "Downregulation of circadian clock gene Period 2 accelerates breast cancer growth by altering its daily growth rhythm," Breast Cancer Res Treat 117:423-31, incorporated herein by reference in its entirety. The Clock and Bmal1 knock-out mice showed altered cell cycle dynamics and premature aging. In addition, the mice show tandem calcifications due in part to the abnormalities in the differentiation and function of the tandem stem cells. See Kondratov R V, Kondratova A A, Gorbacheva V Y, Vykhovanets O V, Antoch M P (2006) "Early aging and age-related pathologies in mice deficient in BMAL1, the core component of the circadian clock," Genes Dev 20:1868-1873 and Antoch M P, Gorbacheva V Y, Vykhovanets O, Toshkov I A, Kondratov R V, Kondratova A A, Lee C, Nikitin A Y (2008) "Disruption of the circadian clock due to the Clock mutation has discrete effects on aging and carcinogenesis," Cell Cycle 7:1197-1204, each incorporated herein by reference in its entirety.

Yang et al in 2011 conducted a study in patient with chronic myeloid leukemia (CML) and looked for the oscillation of the clocks genes in peripheral blood mononuclear cells (PBMCs) and polymorphonuclear (PMNs) cell form these patients compared to healthy individual. They found that the clock is disrupted in the leukemia patients, however treatment with Imatinib restore it in at least 50% of the patients. The study was conducted by withdrawing the blood every four hours from hospitalized patients and volunteers. This study has shown the biological clock is dysregulated in CML patients in which Imatinib has been developed. The study showed that the Clock genes PER1, PER2, PER3, CRY1, CRY2, and CKIε are perturbed in pre-Imatinib treatment and each mentioned gene's expression level returns to normal after treatment. See Yang M Y, Yang W C, Lin P M, Hsu J F, Hsiao H H, Liu Y C, Tsai H J, Chang C S, Lin S F (2011) "Altered expression of circadian clock genes in human chronic myeloid leukaemia," J Biol Rhythms. 136-148, incorporated herein by reference in its entirety. In this regard it may be important to address if the clock is perturbed in CLL patients as well other type of Leukemia, CML and AML.

Chronic lymphocytic leukemia (CLL) is the most common lymphoproliferative disorder characterized by a variable clinical course according to well-defined prognostic factors, such as mutation status of V genes, CD38 and ZAP-70 expression and specific gene profiles. CLL is characterized by the clonal expansion of mature, antigen-stimulated CD5+/CD23+ cells in blood, secondary lymphoid tissues and bone marrow (BM). See Chiorazzi N, Rai K R, Ferrarini M. "Chronic lymphocytic leukemia," N Engl J Med. 2005; 352(8):804-815 and Nagasawa T. "Microenvironmental niches in the bone marrow required for B-cell development," Nat Rev Immunol. 2006; 6(2):107-116, each incorporated herein by reference in its entirety.

For both the early and chronic stage of the CLL, the NGHA clinicians use Imatinib (Gleevec) to treat these patients.

Imatinib is a competitive tyrosine-kinase inhibitor normally used in the treatment of chronic myelogenous leukemia (CML) Gleevec is a specific inhibitors for BCR-Abl tyrosine kinase that is responsible for CML, its half-life and the half-life of its main metabolite are 18 and 40 hours, respectively. See Novartis Pharma A G. "Gleevec® (imatinib mesylate) tablets prescribing information," East Hanover, N.J.; 2006 September Anon. Drugs of choice for cancer. Treat Guide Med Lett. 2003; 1:41-52, incorporated herein by reference in its entirety. It blocks the activity of Abelson cytoplasmic tyrosine kinase (ABL), c-Kit and the platelet-derived growth factor receptor (PDGFR). The inhibition of these kinases by imatinib lead to the blockage of downstream pathways that include the Ras/MapK, JAK/STAT pathway that are responsible for increased cell proliferation. See Weisberg, Ellen; Paul W. Manley, Sandra W. Cowan-Jacob, Andreas Hochhaus, and James Griffin (2007). "Second Generation Inhibitors of BCR-ABL for the Treatment of Imatinib-resistant Chronic Myeloid Leukaemia,". Nature Reviews Cancer 7 7 (5): 345-56, incorporated herein by reference in its entirety.

Although imatinib targets the BCR-Abl, tyrosine kinase has not been directly involved in the manifestation of CLL, but there is a direct link in which the Abl tyrosine kinase is involved in the activation of downstream kinases dysregulated in CLL. See Robak T, Robak E (2012), "Tyrosine kinase inhibitors as potential drugs for B-cell lymphoid malignancies and autoimmune disorders," Expert Opin Investig Drugs. 921-947 and Woyach J. A., Johnson A. J., Byrd J. C. (2012) "The B-cell receptor signaling pathway as a therapeutic target in CLL," Blood 9; 120(6):1175-1184, each incorporated herein by reference in its entirety.

For leukemia patients the oscillation of the biological clock prior and post treatment in both the early and chronic stage of the disease is important for developing a better treatment approach.

In view of the forgoing, one objective of the present disclosure is to provide a method of treating leukemia based on the gene expression of clock genes in a patient.

BRIEF SUMMARY OF THE INVENTION

According to a first aspect, the present disclosure relates to a method of treating leukemia in a patient, the method including obtaining a plasma sample from a patient undergoing a first treatment for leukemia at a first time point and at a second time point, wherein the first time point is before the second time point; measuring a gene expression level of a set of core clock genes, and at least one of a first set of peripheral clock genes and a second set of peripheral clock genes, each in the plasma sample at the first time point and in the plasma sample at the second time point; determining that the first treatment is effective for the patient when the gene expression level of the set of core clock genes in the plasma sample at the second time point relative to the first time point is increased by 1-fold to 18-fold, and the gene expression level of the first set of peripheral clock genes at the second time point relative to the first time point is increased by 1-fold to 3-fold, and the gene expression level of the second set of peripheral clock genes at the second time point relative to the first time point is decreased by 2-fold to 5-fold; and continue treating the patient with the first treatment.

In some implementation of the method, a time gap between the first time point and the second time point is 1 month to 12 months.

In some implementation of the method, the leukemia is at least one of chronic myelogenous leukemia, acute myelogenous leukemia, chronic lymphocytic leukemia, acute lymphocytic leukemia, and mixed lineage leukemia.

In some implementation of the method, the first treatment is at least one treatment selected from the group consisting of imatinib (Gleevec), dasatinib (Sprycel), nilotinib (Tasigna), bosutinib (Bosulif), ponatinib (Iclusig), Busulfan, Cyclophosphamide, and Cytarabine.

In some implementation of the method, the set of core clock genes comprises CLOCK, BMAL1, CRY1, CRY2, and Per2.

In some implementation of the method, the first set of peripheral clock genes comprises a gene of a protein that upregulates the gene expression level of at least one member of the set of core clock genes.

In some implementation of the method, the first set of peripheral clock genes includes at least one of RORα and PPARα.

In some implementation of the method, the second set of peripheral clock genes comprises a gene of a protein that downregulates the gene expression level of at least one member of the set of core clock genes.

In some implementation of the method, the second set of peripheral clock genes includes REV-ERBα.

According to a second aspect, the present disclosure relates to a method of treating leukemia in a patient, the method including obtaining a plasma sample from a patient undergoing a first treatment for leukemia at a first time point and at a second time point, wherein the first time point is before the second time point; measuring a gene expression level of a set of core clock genes, and at least one of a first set of peripheral clock genes and a second set of peripheral clock genes, each in the plasma sample at the first time point and in the plasma sample at the second time point; determining that the first treatment is not effective for the patient when the gene expression level of the set of core clock genes in the plasma sample at the second time point relative to the first time point is decreased by 1-fold to 110-fold, the gene expression level of the first set of peripheral clock genes at the second time point relative to the first time point is decreased by 5-fold to 40-fold, and the gene expression level of the second set of peripheral clock genes at the second time point relative to the first time point is increased by 1-fold to 5-fold; and treating the patient with a second treatment, wherein the second treatment is different from the first treatment.

In some implementations of the method, a time gap between the first time point and the second time point is 1 month to 12 months.

In some implementations of the method, the leukemia is at least one of chronic myelogenous leukemia, acute myelogenous leukemia, chronic lymphocytic leukemia, acute lymphocytic leukemia, and mixed lineage leukemia.

In some implementations of the method, the first treatment and the second treatment is at least one treatment selected from the group consisting of imatinib (Gleevec), dasatinib (Sprycel), nilotinib (Tasigna), bosutinib (Bosulif), ponatinib (Iclusig), Busulfan, Cyclophosphamide, and Cytarabine.

In some implementations of the method, the set of core clock genes comprises CLOCK, BMAL1, CRY1, CRY2, and Per2.

In some implementations of the method, the first set of peripheral clock genes comprises a gene of a protein that upregulates the gene expression level of at least one member of the set of core clock genes.

In some implementations of the method, the first set of peripheral clock genes includes at least one of RORα and PPARα.

In some implementations of the method, the second set of peripheral clock genes comprises a gene of a protein that downregulates the gene expression level of at least one member of the set of core clock genes.

In some implementations of the method, the second set of peripheral clock genes includes REV-ERBα.

According to a third aspect, the present disclosure relates to a method for treating a patient undergoing a first treatment for leukemia having at least one of chronic myelogenous leukemia, acute myelogenous leukemia, chronic lymphocytic leukemia, acute lymphocytic leukemia, and mixed lineage leukemia, the method including continue administering a first treatment to the patient in need thereof or administering a second treatment to the patient in need thereof The patient is selected for administration of the first treatment by a method including obtaining a plasma sample from the patient at a first time point and at a second time point, wherein the first time point is before the second time point and a time gap between the first time point and the second time point is 1 month to 12 months; measuring a gene expression level of a set of core clock genes, and at least one of a first set of peripheral clock genes and a second set of peripheral clock genes, each in the plasma sample at the first time point and in the plasma sample at the second time point; and determining that the first treatment is effective for the patient when the gene expression level of the set of core clock genes in the plasma sample at the second time point relative to the first time point is increased by 1-fold to 18-fold, and the gene expression level of the first set of peripheral clock genes at the second time point relative to the first time point is increased by 1-fold to 3-fold, and the gene expression level of the second set of peripheral clock genes at the second time point relative to the first time point is decreased by 2-fold to 5-fold. The patient is selected for administration of the second treatment, wherein the second treatment is different from the first treatment, by a method including obtaining a plasma sample from a patient at a first time point and at a second time point, wherein the first time point is before the second time point and a time gap between the first time point and the second time point is 1 month to 12 months; measuring a gene expression level of at least two of a set of core clock genes, a first set of peripheral clock genes, and a second set of peripheral clock genes, each in the plasma sample at the first time point and in the plasma sample at the second time point; and determining that a first treatment is ineffective for the patient when the gene expression level of the set of core clock genes in the plasma sample at the second time point relative to the first time point is decreased by 1-fold to 110-fold, the gene expression level of the first set of peripheral clock genes at the second time point relative to the first time point is decreased by 5-fold to 40-fold, and the gene expression level of the second set of peripheral clock genes at the second time point relative to the first time point is increased by 1-fold to 5-fold. The set of core clock genes comprises CLOCK, BMAL1, CRY1, CRY2, and Per2, the set of first peripheral clock genes comprises a gene of a protein that upregulates the gene expression level of at least one member of the set of core clock genes and includes at least one of RORα and PPARα, the set of second peripheral clock genes comprises a gene of a protein that downregulates the gene expression level of at least one member of the set of core clock genes and includes REV-ERBα.

In some implementations of the method, the first treatment and the second treatment is at least one treatment selected from the group consisting of imatinib (Gleevec), dasatinib (Sprycel), nilotinib (Tasigna), bosutinib (Bosulif), ponatinib (Iclusig), Busulfan, Cyclophosphamide, and Cytarabine.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein:

FIG. 9A is an exemplary graph of oscillatory patterns of BMAL1 and Per3 in Donor 1 sample after an attempt to synchronize the patterns with temperature changes;

FIG. 9B is an exemplary graph of oscillatory patterns of BMAL1 and Per3 in Donor 2 sample after an attempt to synchronize the patterns with temperature changes;

FIG. 9C is an exemplary graph of oscillatory patterns of BMAL1 and Per3 in Donor 3 sample after an attempt to synchronize the patterns with temperature changes;

FIG. 9D is an exemplary graph of oscillatory patterns of BMAL1 and Per3 in an average of Donor 1, Donor 2 and Donor 3 samples after an attempt to synchronize the patterns with temperature changes;

DETAILED DESCRIPTION OF THE EMBODIMENTS

Figure 1:
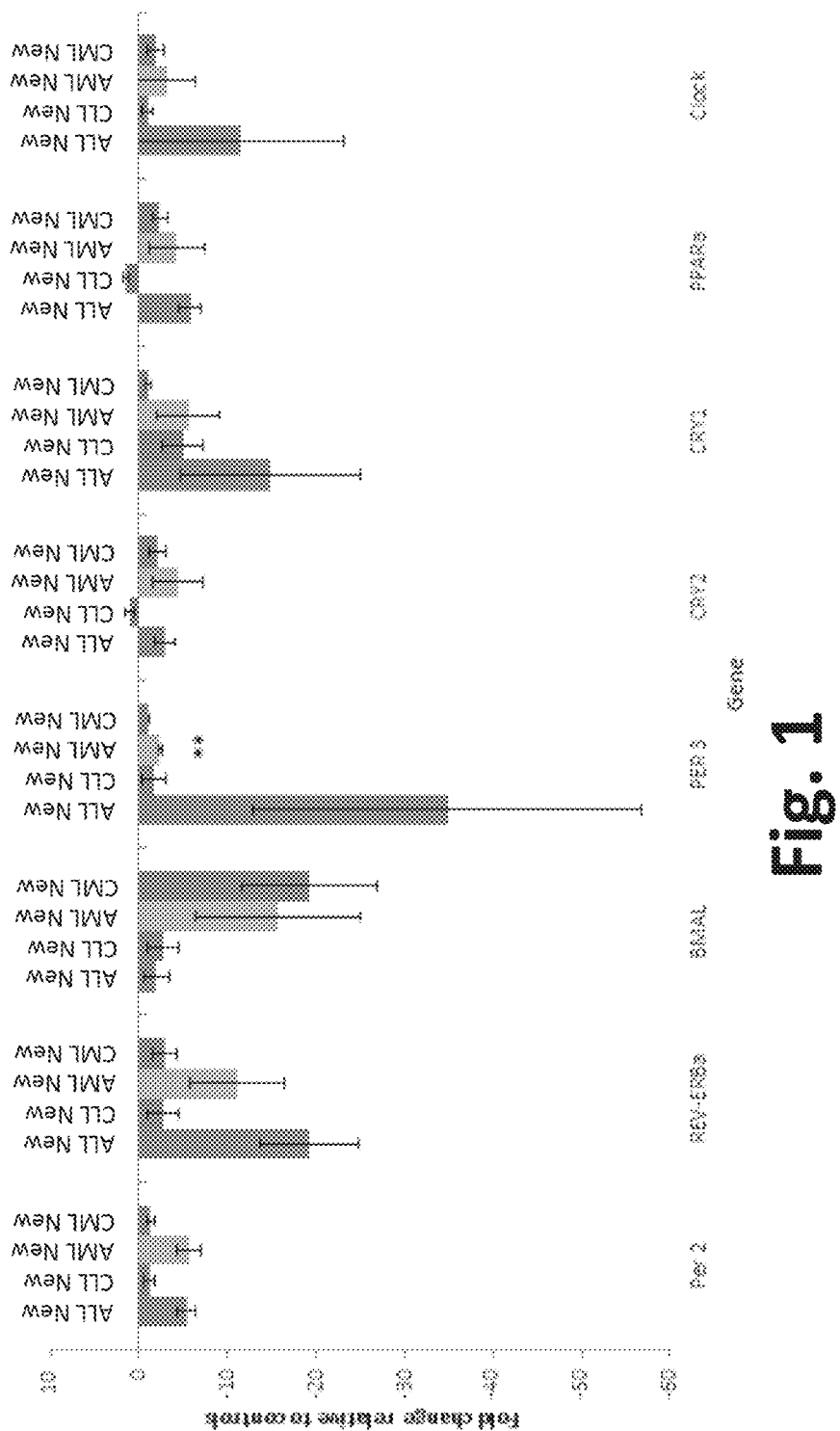
FIG. 1 is an exemplary graph of fold change in gene expression relative to controls in new cases of ALL, CLL, AML, and CML.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Abnormal cell growth", as used herein, unless otherwise indicated, refers to cell growth that is independent of normal regulatory mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "leukemia" refers to an acute or chronic disease of unknown cause in man and other warm blooded animals that involves developing cells of the blood-immune system. Leukemia is characterized by an abnormal increase in the number of leucocytes in the tissues of the body with or without a corresponding increase of those in the circulating blood and is classified according of the type leucocyte most prominently involved. Leukemias were originally termed acute or chronic based on life expectancy but now are classified according to cellular maturity. Acute leukemias consist of predominantly immature cells (usually blast forms); chronic leukemias, more mature cells. Acute leukemias are divided into lymphoblastic (ALL) and myelogenous (AML) types, which may be further subdivided by morphologic and cytochemical appearance according to the French-American-British (FAB) classification or immunophenotype. The specific B-cell and T-cell and myeloid-antigen monoclonal antibodies, together with flow cytometry, are helpful for classifying ALL versus AML, which is important for treatment. Chronic leukemias are described as lymphocytic (CLL) or myelocytic (CML).

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

Throughout the specification and the claims the terms "patient" and "subject" are used interchangeably.

The present disclosure relates to genes which regulate circadian patterns or oscillations. In virtually all light-sensitive organisms from cyanobacteria to humans, a circadian timing system adapts cyclic physiology to geophysical time. In mammals, the cellular oscillation is similar in both SCN and peripheral tissues. It contains the interlocked negative feedback loops. The feedback loops as described herein refer to a mechanism of gene transcriptional regulation. For example, direct interaction with DNA is the simplest and the most direct method by which a protein changes transcription levels. Genes often have several protein binding sites around a coding region in DNA with the specific function of regulating transcription. There are many classes of regulatory DNA binding sites known as enhancers, insulators and silencers. The mechanisms for regulating transcription are varied, from blocking key binding sites on the DNA for RNA polymerase, to acting as an activator and promoting transcription by assisting RNA polymerase binding. Feedback loops may be described in terms of biological circuits, which produce complex outputs by exploiting one or more feedback loops. In a sequence of biochemical events, feedback would refer to a downstream element in the sequence affecting an upstream component to affect its own production or activation (output) in the future. If the element, such as the protein binding sites around a coding region in DNA with the specific function of regulating transcription, acts to enhance its own output, then it engages in positive feedback. A positive feedback loop is also known as a self-reinforcing loop, and it is possible that these loops can be part of a larger loop, as this is characteristic of regulatory circuits. Conversely, if the element leads to its own inhibition through upstream elements, this is canonically negative feedback. A negative feedback loop is also known as a balancing loop, and it may be common to see oscillations in which a delayed negative feedback signal is used to maintain homeostatic balance in the system. In mammals the "clock" (genes of proteins that control the circadian pattern) is composed of two feedback loops: primary and secondary loop. Both are co-regulated by other transcription factors such as nuclear receptors. See Roenneberg T, Merrow M (2005) Circadian clocks—the fall and rise of physiology, Nat Rev Mol Cell Biol 6:965-971; Dunlap J C (1999) Molecular Bases for circadian clocks, Cell 96:271-290; and Gery S., Koeffler, H P (2010) Circadian Rhythms and cancer, Cell Cycle 9:1097-1103.4.3, each incorporated herein by reference in its entirety. In the core or primary clock feedback loop, there are two heterodimeric transcription factors. These include CLOCK/BMAL1 and NPAS2/BMAL1. These complexes are formed by several genes including the Clock gene (circadian locomotors output cycles kaput), NPAS2 gene (Neuronal PAS domain protein 2) and Bmal gene (brain and muscle aryl hydrocarbon receptor nuclear translocator like—Arntl), which represents the central node in a network of clock genes and a transcription initiator of the feedback loops. NPAS2 gene is reported to be highly related in primary amino acid sequence to CLOCK. These two genes (CLOCK and NPAS2) may drive the expression of the Period1/2 and cryptochrome1/2 genes by binding to E-box cis-elements in the promoter regions of the Period 1, 2 and 3 genes (Per1, Per2, and Per3), and Cryptochrome genes (Cry1, Cry2). An "E-box" is a DNA response element which may be found in some eukaryotes that acts as a protein-binding site and has been found to regulate gene expression in neurons, muscles, and other tissues. "Cis-" implies that the E-box element of DNA is present on the same molecule of DNA as the gene which is regulated. In turn, the proteins (PER1/2 and CRY1/2) are reported to heterodimerise and repress the activity of CLOCK and NPAS2 (i.e. this will inhibit the expression of CLOCK and NPAS2 genes.) This mechanism of inhibition is known as a negative PER/CRY feedback loop, which may be commonly recognized as the generator of the circadian rhythm.

The transcription of Period and Cryptochrome genes may be initiated during the circadian day. The transcription of Period and Cryptochrome genes is supported by posttranslational modifications. PER and CRY proteins may enter the nucleus as a multimeric complex (PER/CRY) to inhibit CLOCK/BMAL-mediated transcription. During the night cycle, the PER/CRY complex is degraded, thus the inhibitory effect on CLOCK/BMAL will be released; therefore allowing the progression of a new cycle of transcription. See Zhang E E, Kay S A (2010) Clocks not winding down: unravelling circadian networks Nat Rev Mol Cell Biol 11:764-776, incorporated herein by reference in its entirety.

The molecular clock adapts its function in certain cell types with a secondary feedback loop that involves other transcription factors and posttranslational modification loops. The best characterized loop so far, is the secondary loop orchestrated by REV-ERBs and RORα nuclear receptors. See Schmutz I, Ripperger J A, Baeriswyl-Aebischer S, Albrecht U (2010) The mammalian clock component PERIOD2 coordinates circadian output by interaction with nuclear receptors. Genes Dev 24:345-357, incorporated herein by reference in its entirety.

The REV-ERBs (REV-ERBα and REV-ERBβ) are known as orphan nuclear receptors that may be expressed in adipose tissue, skeletal muscle, brain and liver. REV-ERBβ may be expressed in parts of the brain, thyroid, uterus and pituitary, whereas REV-ERBα is highly expressed in immune cells, such as macrophages. REV-ERBs are reported as transcriptional repressors because of a lack of activation-function 2 (AF-2) region which is involved in coactivator binding that allow them to bind co-repressor proteins such as the nuclear receptor corepressor (NCoR). See Duez H and Staels B (2008) The Nuclear Receptors Rev-Erbs and RORs integrate circadian rhythms and metabolism. Diabetes and Vascular Disease Research 5:82-88.

In contrast to REV-ERBs, ROR (Retinoid Orphan Receptor) subfamily nuclear receptors are transcription activators. Several members of this subfamily have been discovered including RORα, RORβ and RORγ. All have sequence similarities to the retinoic acid receptors (RARs) and the RXRs. See Carlberg C, Hooft van Huijsduijnen R, Staple J K, DeLamarter J F, Becker-André M (1994) RZRs, a new family of retinoid-related orphan receptors that function as both monomers and homodimers. Mol Endocrinol 8:757-770 and Hirose T, Smith R J, Jetten A M (1994) ROR gamma: the third member of ROR/RZR orphan receptor subfamily that is highly expressed in skeletal muscle. Biochem Biophys Res Commun 205:1976-1983, each incorporated herein by reference in its entirety.

RORα is expressed in liver, skeletal muscle, skin, lungs, adipose tissue, kidney, thymus and brain while the expression of RORβ is restricted to the CNS. In addition, RORγ is found primarily in the immune tissues, liver, skeletal muscle, adipose tissue and kidney. See Jetten A M. (2009) Retinoid-related orphan receptors (RORs): important roles in development, immunity, circadian rhythm, and cellular metabolism. Nucl Recept Signal. 2009; 7:e003, incorporated herein by reference in its entirety.

As discussed above, the RORα and REV-ERBα form a component of the secondary feedback loop of the circadian clock. Therefore, RORα and REV-ERBα may be regulators of the cyclic expression of BMAL1 and CLOCK. In addition, the REV-ERBα transcription is reported to be activated by the BMAL1/CLOCK heterodimer and trans-repressed by CRY/PER, resulting in circadian oscillations of REV-ERBα. In turn, REV-ERBα represses BMAL1 and CLOCK transcription. REV-ERBβ expression also oscillates in a circadian fashion and can repress BMAL1 transcription. RORα competes with REV-ERBα for binding of their shared RORE DNA binding elements in the BMAL1 promoter leading to BMAL1 expression being repressed by REVERBα and activated by RORα. The oscillating expression of RORα and REV-ERBα in the SCN may lead to the circadian pattern of BMAL1 expression. This REV-ERBα/RORα feedback loop interconnects the positive and negative limbs of the core circadian clock. See Harding H P, Lazar M A (1995) The monomer-binding orphan receptor REV-ERB represses transcription as a dimer on a novel direct repeat. Mol Cell Biol 15:4791-4802, incorporated herein by reference in its entirety.

NPAS2, like CLOCK, forms heterodimers with BMAL1 and effectively functions in the regulation of mammalian circadian rhythms. NPAS2, like BMAL1, is a RORα and REV-ERBα target gene. NPAS2 promoter has an RORE binding element and demonstrated that both RORα and REVERBα regulate the expression of NPAS2, thus suggesting a mechanism by which RORα and REV-ERBα coordinately regulate the positive limb of the circadian clock. See Guillaumond F, Dardente H, Giguère V, Cermakian N (2005) Differential control of Bmal1 circadian transcription by REV-ERB and ROR nuclear receptors. J Biol Rhythms 20:391-403; Sato T K, Panda S, Miraglia L J, et al. (2004) A functional genomics strategy reveals Rora as a component of the mammalian circadian clock. Neuron 43:527-537; Akashi M, Takumi T (2005) The orphan nuclear receptor RORα regulates circadian transcription of the mammalian core-clock Bmal1. Nat Struct Mol Biol. 12:441-448; and Solt L A, Kojetin D J, Burris T P (2011) The REV-ERBs and RORs: molecular links between circadian rhythms and lipid homeostasis. Future Med Chem 3:623-638, each incorporated herein by reference in its entirety.

The present disclosure relates to a method of treating leukemia in a patient. The method includes obtaining a plasma sample from a patient undergoing a first treatment for leukemia at a first time point and at a second time point, wherein the first time point is before the second time point. For example, the presently describe method may be used to treat a patient before the patient begins the first treatment (i.e. before a diagnosis of leukemia), after the patient undergoes a first treatment (i.e. after a diagnosis of leukemia and the first treatment regimen has begun), or for a patient who has successfully completed a first round of treatment. The first time point and the second time point may have a time gap of 1 month-12 months, 2 months-10 months, or preferably 3 months-6 months. The time gap may be shorter as per a physician's recommendation for the patient. In some implementations of the method, the first time point is before a first treatment and the second time point is after the first treatment. In addition to treating leukemia in a patient currently undergoing treatment, the method described herein may be used to treat leukemia in a patient that has not been previously treated for leukemia. For example, the sample taken from a patient at a first time point may be before a patient has started a treatment plan for leukemia, and the second sample taken from the patient at a second time point may be after the patient has begun the treatment plan for leukemia.

Plasma samples may be obtained by phlebotomy methods known in the art. Plasma samples may be obtained from whole blood. In some embodiments, serum, plasma or both are employed in the method. Within the plasma, sample cells from which the gene expression levels may be measured include peripheral blood mononuclear cells (PBMC) and polymorphonuclear (PMN) cells. PBMC may be any peripheral blood cell having a round nucleus. These cells include lymphocytes (T cells, B cells, NK cells) and monocytes whereas erythrocytes and platelets have no nuclei, and neutrophils, basophils, and eosinophils have multi-lobed nuclei. In general, biological samples (e.g. tissue samples, serum samples, urine samples, saliva samples, blood samples or biopsy samples) may be obtained from the individual to have gene expression at mRNA or protein levels compared to that in the sample at the first time point or from a non-leukemia patient (i.e. a normal tissue sample).

The normal tissue samples may be obtained from the same individual who is to be tested for a disease status at a date prior to diagnosis with leukemia and prior to administration of the treatment. A sample of blood drawn from the patient may be 35 mL-60 mL or 40 mL-55 mL. The blood sample may be placed into a centrifuge tube and centrifuged to separate PBMC or PMN cells. The centrifugation may be from 10 minutes to 15 minutes or 12 minutes to 13 minutes at a g-force of 500× g to 850× g, 550× g to 800× g, 600× g to 750× g, or 650× g to 700× g. Upon centrifugation the cells in the tube are separated from the supernatant and the cells may be transferred by resuspension in a buffered saline (i.e. phosphate buffered saline from pH 6.5-7.5, or preferable pH 6.9-7.2). The cells may be optionally transferred into new centrifugal tubes for another round of centrifuge and separation. The cells may be proliferated by placement into petri dishes and incubated with growth media for 6 hours-12 hours or 8 hours to 10 hours. The cells may further be induced to proliferate with sorbitol of 0.1-0.5 M or 0.2-0.4 M sorbitol. The induction may be no more than 45 minutes, no more than 30 minutes, or no more than 15 minutes. The cells may be detached from the petri dishes, separated from the media by centrifugation, as described herein, then the cells may be lysed, by detergents and methods known in the art, to release the internal mRNA and DNA for PCR analysis of the gene expression.

Following obtaining the samples, the samples are measured for a gene expression level of a set of core clock genes, a first set of peripheral clock genes, and a second set of peripheral clock genes, each in the plasma sample, obtained as described herein, at the first time point and in the plasma sample at the second time point. The set of core clock genes may include, but is not limited to include core clock genes CLOCK, BMAL1, CRY1, CRY2, PER1, PER2, PER3, NPAS2. The first set of peripheral clock genes includes a gene of a protein that upregulates the gene expression level of at least one member of the set of core clock genes. The first set of peripheral clock genes may include, but is not limited to peripheral clock genes RORα and PPARα. The second set of peripheral clock genes includes a gene of a protein that downregulates the gene expression level of at least one member of the set of core clock genes. The second set of peripheral clock genes may include, but is not limited to peripheral clock genes REV-ERBα and REV-ERBβ. CK1δ and CK1ε are two genes for proteins which upregulate some core clock genes and downregulate some core clock genes. Thus CK1δ and CK1ε may be a member of either the first set of peripheral clock genes or the second set of peripheral clock genes. For example, CK1ε may upregulate BMAL1, however also may downregulate PER1 and PER2. The gene expression of the core and peripheral clock genes described herein may be measured by isolating the RNA by Northern blot analysis employing fluorescently labeled or radiolabeled RNA. The RNA may be removed from the Northern blot gel and purified and eluted in a RNA column as commonly known in the art. Upon isolation of the RNA, the yield and purity of the RNA may be determined by spectrometers, such as the Nanodrop 800 (ThermoScientific). Finally gene expression may be measured, as described elsewhere herein, by DNA microarray, hierarchical cluster analysis, and real-time PCR (RT-qPCR).

In some implementations of the method at least one core clock gene's expression level is measured (the core clock gene being selected from the set of core clock genes), and at least one peripheral clock gene's expression level is measured (the peripheral clock gene being selected from either the first set of peripheral clock genes or the second set of peripheral clock genes, or both). In some implementations of the method, at least one core clock gene's expression level is measured as described herein, and at least one peripheral clock gene's expression level is measured, the peripheral clock gene being selected from either the first set of peripheral clock genes or the second set of peripheral clock genes, or both, and a non-core clock gene expression level may be measured.

The measuring is followed by a determination of the effectiveness of the first treatment when the gene expression measurements correlate with a particular pattern. The first treatment is determined to be effective for the patient when the gene expression level of at least one member of the set of core clock genes in the plasma sample at the second time point relative to the first time point is increased by 1-fold to 18-fold, 2-fold to 16-fold, 4-fold to 14-fold, or 6-fold to 12-fold; the gene expression level of the first set of peripheral clock genes at the second time point relative to the first time point is increased by 1-fold to 3-fold, 1.5-fold to 2.5-fold, or 1.75-fold to 2.25-fold; and the gene expression level of the second set of peripheral clock genes at the second time point relative to the first time point is decreased by 2-fold to 5-fold, 3-fold to 4-fold, or 3.5-fold to 3.75-fold.

Based on the correlations listed above, the first treatment for the patient is advantageously continued by a physician. Therefore the proceeding step in the method is to continue treating the patient with the first treatment. For example, when the patient is treated with Gleevec and whose gene expression follows the described correlation above, then the patient should continue to be prescribed Gleevec. In some implementations, the first treatment is continued at the same dosage and frequency or regimen. In some implementations, the first treatment is continued, however the dosages and/or the regimen may be changed. For example, a physician may choose to continue to prescribe Gleevec to a patient, when the correlations indicate that Gleevec is an effective first treatment, but the physician may choose to increase or decrease the dosage, increase or decrease the frequency of the dosage, or supplement the Gleevec with an additional therapeutic. Further, in some implementations, a physician may choose to add another cancer therapy to the first treatment to bolster effectiveness further, such as surgery, immunotherapy, targeted therapy, hormone therapy, stem cell therapy, or radiotherapy. For example, while a physician may continue Gleevec, the physician may also recommend a dose of immunotherapy. In some embodiments, the patient may have additional treatments added to address non-leukemia disorders, such as depression, anxiety, nausea, migraines, weight disorder, skin disorders, digestive disorders, neurological disorder, sleep disorders, and the like. Exemplary medications that may be added to the patient's regimen may include, but are not limited to citalopram, fluoxetine, paroxetine, anastrozole, toremifene, megestrol, pregabalin, and gabapentin.

An aspect of the present disclosure further relates to method treating the patient with leukemia in the case that the patient's gene expression levels of the measured genes (i.e. the set of core clock genes, the first set of peripheral clock genes, and the second set of peripheral clock genes) are indicative of a relapsed disease. A relapse may be interpreted as a disease returning to previous levels of tumor cells in the blood or tumor growth rate and size prior to the patient receiving a first treatment or a new indication of the disease previously undiagnosed. As such, the first treatment may be determined to be ineffective when the gene expression level of the set of core clock genes in the plasma sample at the second time point relative to the first time point is decreased by 1-fold to 110-fold, 2-fold to 100-fold, 5-fold to 90-fold, 10-fold to 80-fold, 20-fold to 70-fold, 30-fold to 60-fold, or 40-fold to 50-fold; the gene expression level of the first set of peripheral clock genes at the second time point relative to the first time point is decreased by 5-fold to 40-fold, 7-fold to 35-fold, 12-fold to 30-fold, 15-fold to 25-fold, 20-fold to 22-fold; and the gene expression level of the second set of peripheral clock genes at the second time point relative to the first time point is increased by 1-fold to 5-fold or 2-fold to 4-fold. Based on the correlations listed above, the treatment to the patient may be changed to a second treatment, wherein the second treatment is different from the first treatment. Various treatments which may be employed as the first or the second treatment are described herein. In some implementations of the method, the patient may not have had the first treatment, thus the second treatment may be any treatment listed herein.

The presently disclosed methods may be applicable to forms of leukemia including chronic myelogenous leukemia, acute myelogenous leukemia, chronic lymphocytic leukemia, acute lymphocytic leukemia, mixed lineage leukemia, acute promyelocytic leukemia, hairy cell leukemia, myeloblastic leukemia, monocytic leukemia, monocytic leukemia, erythroleukemia, and megakaryocytic leukemia.

Another aspect of the present disclosure relates to a method to treat a patient having at least one of chronic myelogenous leukemia, acute myelogenous leukemia, chronic lymphocytic leukemia, acute lymphocytic leukemia, and mixed lineage leukemia, the method including administering a first treatment to the subject in need thereof, wherein the subject is selected by a method as described herein resulting in the determination that the first treatment is effective and therefore may be continued, or administering a second treatment to the subject in need thereof, wherein the patient is selected by a method as described herein resulting in the determination that the first treatment was ineffective and therefore the second treatment, different from the first treatment, may be administered to the patient. Further, the determination that the first treatment is ineffective may include a scenario wherein the patient is undiagnosed with one of the leukemia types described above and once the patient is diagnosed a treatment is administered. The treatment may be administered in doses known in the art. For example the dose for Gleevec is 200 mg/day-800 mg/day, with two equal doses of half the total dose per day with a gap of 3-8 hours between doses. Doses may be administered at a clinicians orders or based on a pharmaceutically companies directive for the specific treatment.

The first treatment and/or the second treatment may be at least one treatment selected from the group consisting of imatinib (Gleevec), dasatinib (Sprycel), nilotinib (Tasigna), bosutinib (Bosulif), ponatinib (Iclusig), Busulfan, Cyclophosphamide, and Cytarabine. For example, if the first treatment is Gleevec, then the second treatment must be selected from the previously un-selected drugs such as dasatinib, nilotinib, bosutinib, ponatinib, busulfan, cyclophosphamide, and cytarabine. Further, the physician may choose a treatment that differs in its mode of action for the second treatment. For example, if the first treatment is imatinib, a tyrosine kinase inhibitor, then the second treatment may not be a tyrosine kinase inhibitor, such as cyclophosphamide which modifies DNA by alkylation of the guanine base.

Imatinib, or Gleevec, is a type of biological therapy called a tyrosine kinase inhibitor (TKI). Tyrosine kinases are proteins that cells use to signal to each other to grow. They act as chemical messengers. There are a number of different tyrosine kinases and blocking them stops, or reduces, the cancer cells growing. Imatinib targets different tyrosine kinases, depending on the type of cancer. For example, In Ph-positive (Philadelphia chromosome-positive) CML cells, one tyrosine kinase enzyme, BCR-Abl, is constitutively active (i.e. stuck on the "on" position), and continuously may add phosphate groups to activate downstream proteins and enzymes. Imatinib blocks this BCR-Abl enzyme, and stops BCR-Abl from adding phosphate groups to substrate proteins and enzymes.

Dasatinib is an oral Bcr-Abl tyrosine kinase inhibitor and Src family tyrosine kinase inhibitor approved for use in patients with chronic myelogenous leukemia (CML) and Philadelphia chromosome-positive acute lymphoblastic leukemia (Ph+ ALL). Dasatinib Anhydrous is an orally bioavailable synthetic small molecule-inhibitor of SRC-family protein-tyrosine kinases. Dasatinib binds to and inhibits the growth-promoting activities of these kinases. Reportedly, because of its less stringent binding affinity for the BCR-ABL kinase, dasatinib has been shown to overcome the resistance to imatinib of chronic myeloid leukemia (CML) cells harboring BCR-ABL kinase domain point mutations. SRC-family protein-tyrosine kinases interact with variety of cell-surface receptors and participate in intracellular signal transduction pathways; tumorigenic forms can occur through altered regulation or expression of the endogenous protein and by way of virally-encoded kinase genes.

Nilotinib in the form of the hydrochloride monohydrate salt, is a small-molecule tyrosine kinase inhibitor approved for the treatment of imatinib-resistant chronic myelogenous leukemia. Structurally related to imatinib, nilotinib was developed based on the structure of the Abl-imatinib complex to address imatinib intolerance and resistance. Nilotinib is a selective Bcr-Abl kinase inhibitor that is 10-30 fold more potent than imatinib in inhibiting Bcr-Abl tyrosine kinase activity and proliferation of Bcr-Abl expressing cells.

Bosutinib is an ATP-competitive Bcr-Abl tyrosine-kinase inhibitor with an additional inhibitory effect on Src family kinases (including Src, Lyn and Hck). Bosutinib inhibited 16 of 18 imatinib-resistant forms of Bcr-Abl expressed in murine myeloid cell lines.

Ponatinib is a multi-targeted tyrosine-kinase inhibitor. Some forms of CML, those that have the T315I mutation, are resistant to current therapies such as imatinib. Ponatinib has been designed to be effective against tumors having the T315I mutation.

Busulfan is a bifunctional alkylating agent. It destroys cancerous cells by interfering with the DNA in cancer cells, via intrastrand crosslinks at 5'-GA-3' and 5'-GG-3', thereby preventing cancer cells from further dividing and ultimately leading to cell death through apoptosis. DNA adduct repair through dealkylation using the DNA repair enzyme O(6)-alkylguanine DNA alkyltransferase (AGT), encoded by the gene MGMT, can lead to resistance for clinical alkylating agents.

Cyclophosphamide is an alkylating agent of the nitrogen mustard type (specifically, the oxazaphosphorine group). An alkylating agent adds an alkyl group to DNA. The alkylating agent attaches the alkyl group to a guanine base of DNA, at the number 7 nitrogen atom of the imidazole ring. This interferes with DNA replication by forming intrastrand and interstrand DNA crosslinks.

Cytarabine kills cancer cells by interfering with DNA synthesis. It is called a cytosine arabinoside because it combines a cytosine base with an arabinose sugar. Cytosine normally combines with a different sugar, deoxyribose, to form deoxycytidine, a component of DNA. Certain sponges, where it was originally found, use arabinoside sugars to form a different compound (not part of DNA). Cytosine arabinoside is similar enough to human cytosine deoxyribose (deoxycytidine) to be incorporated into human DNA, but different enough that it kills the cell. This mechanism is used to kill cancer cells. Cytarabine is the first of a series of cancer drugs that altered the sugar component of nucleosides. Other cancer drugs modify the base.

In some implementations of the method, the first treatment and/or the second treatment may include a variety of therapies for cancer including, but not limited to stem cell therapy, surgery, immunotherapy, radiation therapy, and hormonal therapy. Further, the chemotherapy treatments as described herein, may further include pharmaceutical treatments for cancer that block angiogenesis, treatments that interfere with mitosis (anti-microtubule agents, DNA alkylating agents, anti-metabolites, topoisomerase inhibitors), treatments that inhibit enzymatic pathways that interfere with mitosis (kinase and phosphatase inhibitors), and ATPase or GTPase inhibitors. The previously listed therapies may be included in combination with the chemotherapies specific to treating leukemia.

In some implementations, the first or second treatment may include combinations of therapy. For example the first treatment may involve a combination of surgery and imatinib, and the second treatment may involve radiation therapy and dasatinib.

In the above method, gene expression levels may be measured by DNA microarray and hierarchical cluster analysis, real-time PCR (RT-qPCR), or northern analysis. Other methods of quantitative gene expression measurement may be found in U.S. Pat. No. 5,643,765 A, incorporated herein by reference in its entirety.

The DNA microarray method employs a collection of microscopic DNA spots attached to a solid surface. Scientists use DNA microarrays to measure the expression levels of large numbers of genes simultaneously or to genotype multiple regions of a genome. Each DNA spot contains picomoles ($10^{-12}$ moles) of a specific DNA sequence, known as probes (or reporters or oligos). These can be a short section of a gene or other DNA element that are used to hybridize a cDNA or cRNA (also called anti-sense RNA) sample (called target) under high-stringency conditions. Probe-target hybridization is usually detected and quantified by detection of fluorophore-, silver-, or chemiluminescence-labeled targets to determine relative abundance of nucleic acid sequences in the target.

mRNA quantitation by northern blotting may occur by a sample of RNA separated on an agarose gel then hybridized to a radioactively labeled RNA probe that is complementary to a target sequence. The radiolabeled RNA may then be detected by an autoradiograph. Because the use of radioactive reagents may create hazardous conditions, alternative labeling and detection methods, such as digoxigenin and biotin chemistries, have been developed and may be employed. Perceived disadvantages of northern blotting may be that large quantities of RNA are required and that quantification may not be completely accurate, as it involves measuring band strength in an image of a gel. On the other hand, the additional mRNA size information from the Northern blot allows the discrimination of alternately spliced transcripts which may indicate variations on the mRNA or irrelevant mRNA samples.

In Quantitative PCR, DNA amplification is monitored at each cycle of PCR. When the DNA is in the log linear phase of amplification, the amount of fluorescence increases above the background. The point at which the fluorescence becomes measurable is called the Threshold cycle ($C_T$ or $C_t$) or crossing point. By using multiple dilutions of a known amount of standard DNA, a standard curve can be generated of log concentration against $C_T$. The amount of DNA or cDNA in an unknown sample can then be calculated from its $C_T$ value.

RT-qPCR employs reverse transcription from mRNA and followed by quantitative PCR. Reverse transcription first generates a DNA template from the mRNA; this single-stranded template is called cDNA. The cDNA template is then amplified in the quantitative step, during which the fluorescence emitted by labeled hybridization probes or intercalating dyes changes as the DNA amplification process progresses. With a carefully constructed standard curve, qPCR can produce an absolute measurement of the number of copies of original mRNA, typically in units of copies per nanoliter of homogenized tissue or copies per cell.

In some implementations of the presently described method, the patient may have multiple diseases in addition to leukemia, as described herein. For example, the patient may have leukemia and at least one of hepatitis, myelofibrosis, arthritis, gout or the like.

In some implementations of the method when determining the effectiveness of the first treatment the first time point may be unavailable. In such a scenario the sample of the first time point may be substituted with a statistically normalized sample for non-leukemic patients for comparison to the sample of the second time point. In some embodiments, the sample at the first time point may be taken from the patient before the administration of the first treatment and the sample at the second time point may be taken from the patient after administration of the first treatment. The methods described herein may be repeated as many times as necessary to treat the patient.

The examples below are intended to further illustrate the method of the present disclosure and are not intended to limit the scope of the claims.

Example 1

Blood Sampling from Patients:

Blood was taken from early stage and chronic CLL, CML and AML patients four times: One prior to treatment, the second after 3 months of treatment, the third after 6 months of treatment and the fourth after 12 months or after the completion of the treatment. Each time 40-50 ml of blood was withdrawn by a trained phlebotomist nurse following NGHA standard rules.

PBMC Purification and Cell Induction

Whole blood (Patient or control) from EDTA tubes using was transferred using a 5 ml pipette into a 50 ml Falcon tube. To this tube, an equal volume of PBS was added (1:1, PBS: Blood) and the tube mixed several times by inverting. The blood/PBS mix tube was then transferred into 2×50 ml LeucoSep® tubes (Greiner Bio One, VWR). The tubes were then centrifuged at room temperature (18-20° C.) for 15 minutes at 800×g with the brake turned off and acceleration at 2 minutes followed by deceleration at zero minutes. Following centrifugation, the white cell interface (buffy coat) was removed using a Pasteur pipette and transferred to a fresh 50 ml centrifuge tube. Care was taken while retrieving the cells from the interface as any disturbance of the red cell pellet at the bottom of the ficoll layer (a highly branched, hydrophilic polysaccharide) could have led to cell contamination. Next, PBS was added to the tube containing the white cell interface up to a total volume of 25 ml. An equal volume of PBS was usually added, however if this was not possible in a single tube then the volume was divided equally into two separate 50 ml Falcon tubes. The tubes were centrifuged for 10 minutes at room temperature at 400×g with the brake off and acceleration at 4 minutes and deceleration at 2 minutes. The supernatants were then carefully aspirated from the pellet using a vacuum pump. Cell pellets were then re-suspended in a small volume of PBS, and then to each tube PBS was added to a total volume of 20 mls. The cells were then centrifuged for 5 minutes at room temperature at 400×g with the brake off and acceleration at 4 minutes and deceleration at 2 minutes. The supernatant from the pellet was then carefully aspirated and discarded in an appropriate manner. The cells were then re-suspended in 5 ml PBS and counted using the Vi-Cell automated cell counter.

A 6-well plate was seeded at a concentration of 2×6 cells per well in complete media (RPMI-1640 plus 10% FBS, 1% Penicillin-Streptomycin, 1% L-glutamine, 1% MEM Non-Essential Amino Acids Solution). After an overnight incubation, the cells were treated for 30 minutes with 0.3 M sorbitol to induce cell proliferation. Following 30 minutes of incubation, the media (with cells) was removed and centrifuged at 500×g for 10 minutes. Following centrifugation, the supernatant was removed and the cell pellet re-suspended in cell-lysis buffer and immediately processed for quantification or alternatively the cell lysates were frozen at −80° C. for later use.

RNA Isolation and QPCR

Total RNA from thawed PBMC pellets was isolated using the SV Total RNA Isolation kit (Promega) according to manufacturer's recommendations. Elution of RNA was performed in 50 µl of RNase-free water and RNA yield and purity was measured using the Nanodrop 8000 spectrophotometer (ThermoScientific). For reverse-transcription, 400 ng of purified RNA was made up in a total volume of 10 µl and reverse transcribed using the High Capacity cDNA Reverse transcription kit (Applied Biosystems) in a final reaction volume of 20 µl according to the manufacturer's recommendation using the Veriti 96-well Thermal cycler system (ThermoScientific). For Taqman Quantitative real-time PCR, 1 ul of cDNA was quantified in the presence of Taqman Universal master mix (Applied Biosystems) and gene/probe sets to a total volume of 5 µl using the 7900HT Fast Real-time PCR system (Applied Biosystems). All Taqman gene expression assays were purchased from Applied Biosystems and assays were performed in a MicroAmp optical 384-well reaction plate (Applied Biosystems). Relative mRNA abundance form duplicate samples was calculated using the $\Delta\Delta C_t$ method and fold change in gene expression was measured relative to control samples. In-sample normalization was performed using GAPDH.

The expression of clock genes is down regulated in patients newly diagnosed with leukemia:

In order to better understand the relationship between leukemia and the clock genes, we assessed the expression of the main core clock genes (BMAL1, CLOCK, PER2, PER3, CRY1 and CRY2 genes) as well as peripheral clock genes (REV-ERBα, RORα and PPARα genes) in a number of patients across four different categories of leukemia: AML, ALL, CML and CLL. For this purpose, PBMC samples were derived from patients who were either newly diagnosed with the disease or who were undergoing treatment.

As shown in FIG. 1, the expression of all clock genes, both core and peripheral were down-regulated in AML, ALL, CML and CLL patients. The extent of this down regulation differed across the genes. The most down-regulated gene in newly diagnosed patients in both the AML and CML disease categories was BMAL1. However, in patients newly diagnosed with ALL, REV-ERBα was the gene that was most down-regulated as well as being highly down-regulated in patients newly diagnosed with CML.

FIG. 1 depicts the data resulting from quantitative real-time PCR expression profiling of the circadian clock genes in Peripheral Blood Mononuclear Cells (PBMCs) derived from newly diagnosed Acute and Chronic Lymphoid leukemia (ALL; CLL respectively) and Acute and Chronic Myeloid leukemia (AML; CML respectively) patients. Expression of the eight circadian clock genes in PBMCs from 5 patients newly diagnosed either with ALL or CML, 6 patients newly diagnosed with either AML or CLL, and 10 control samples from healthy individuals were determined. In comparison to control samples, the expression of Period 3 (PER3) was significantly down-regulated (p<0.01) in newly diagnosed CML patients. The y-axis represents the fold change in mRNA expression levels in patients relative to healthy control samples. The relative expression in patients was determined using the comparative $C_t$ ($\Delta\Delta C_t$ method). The mean mRNA expression in healthy individuals (n=10) was designated a value of 1, whereas the level of mRNA expression in patients with ALL, CLL, AML or CML was calibrated to obtain a fold-change in expression relative to controls. Statistically significant at *p<0.01.

Figure 2:
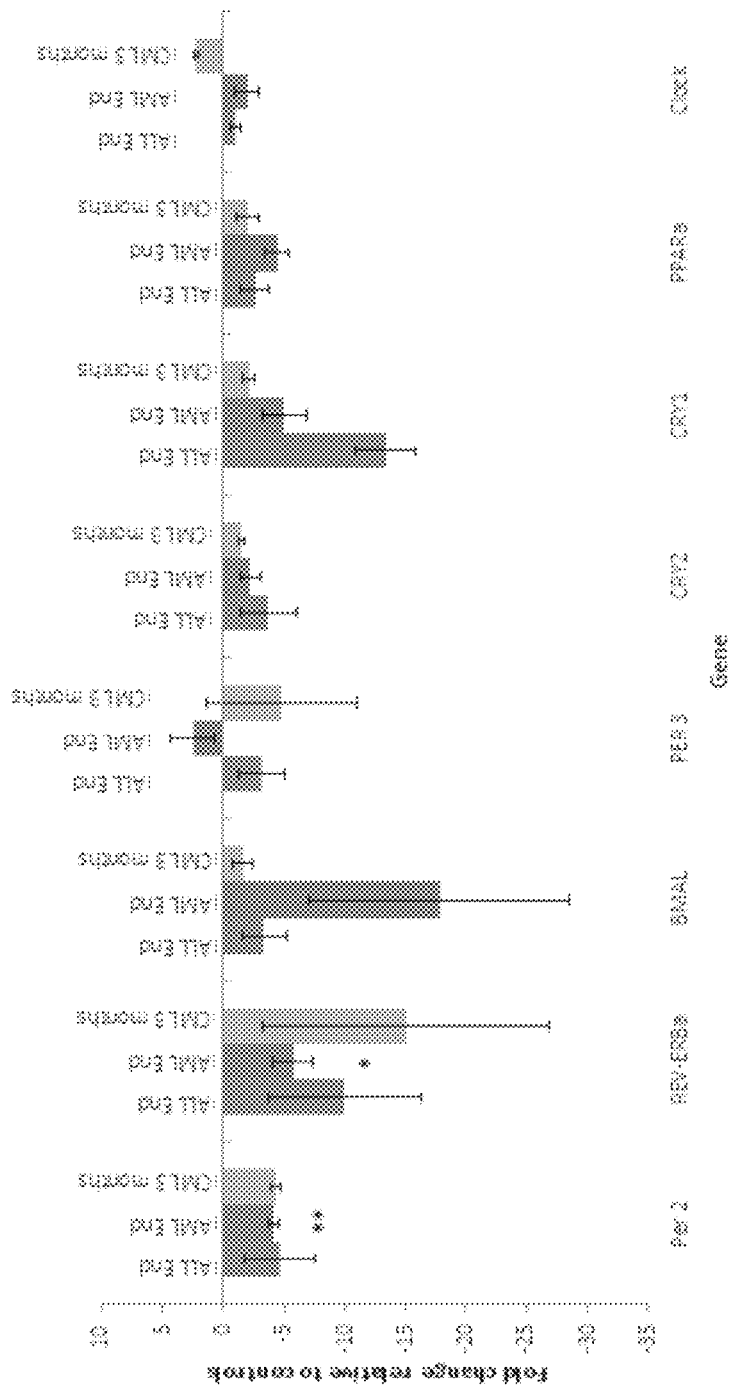
FIG. 2 is an exemplary graph of fold change in gene expression relative to controls in the end of treatments for ALL, AMD and cases of CML at the end of 3 months of treatment.

The upregulation of PER3 in AML patients at the end of treatment is an indication of patient recovery and up regulation of CLOCK is an indication of treatment in CML:

The expression of clock genes was followed in patients that had completed their course of treatment for AML and ALL and those that were still under treatment for CML. As shown in FIG. 2. The PER3 gene was up-regulated in AML patients that had completed treatment, and the CLOCK gene was up-regulated in CML patients after 3 months of treatment.

The significance of these findings may be that the expression of the clock genes PER3 and CLOCK may assist in making a determination of treatment efficacy and patient recovery.

Figure 3:
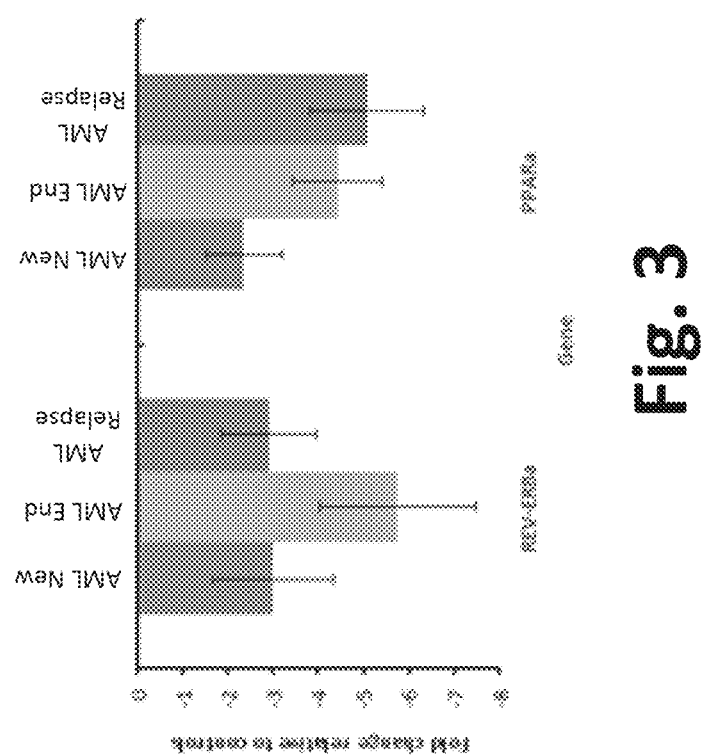
FIG. 3 is an exemplary graph of fold change in gene expression relative to controls in new cases of AML, at the end of AML treatment, and AML relapsed cases.

Analysis of REV-ERBα and PPARα expression in AML patients upon disease diagnosis, at the conclusion of treatment and during relapse of the disease:

FIG. 3 depicts the changes in peripheral clock gene expression in AML patients at the point of disease diagnosis, after a course of chemotherapy treatment and upon relapse of the disease. Gene expression was performed by qPCR using the ΔΔCt method using control samples as calibrant. Data was expressed as a fold change in ΔΔCt relative to the control samples which were given a value of 1.

Figure 4:
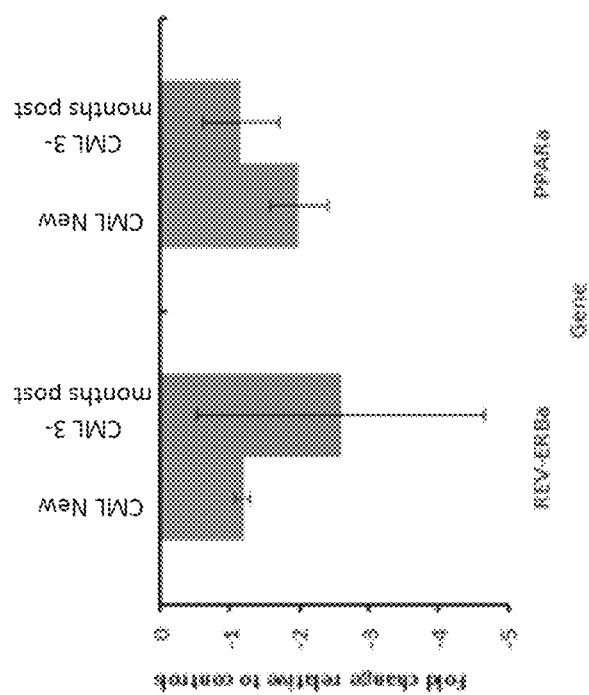
FIG. 4 is an exemplary graph of fold change in peripheral clock gene expression relative to controls in new cases of CML and cases of CML at the end of 3 months of treatment.

Both peripheral clock genes (REV-ERBα and PPARα) show down-regulation in expression relative to control samples. During disease relapse, REV-ERBα expression reverts back to what it was during the initial diagnosis. These patterns of expression in the peripheral clock genes open up the possibility of these being used as clinical biomarkers to determine treatment efficacy or to see whether the patient is on the verge of relapsing. Changes in REV-ERBa and PPARa gene expression in CML patients upon disease diagnosis and at the conclusion of treatment:

FIG. 4 depicts the changes in peripheral clock gene expression in CML patients at the point of disease diagnosis, and three months post-treatment. Gene expression was performed by qPCR using the ΔΔCt method using control samples as calibrant. Data was expressed as a fold change in ΔΔCt relative to the control samples which were given a value of 1.

Both peripheral clock genes tested (REV-ERBα and PPARα) showed different patterns of expression in CML patients upon diagnosis of the disease and after a course of chemotherapy treatment. REV-ERBα showed further down-regulation at the conclusion of treatment whereas PPARα showed a reduced down-regulation after treatment relative to control samples. This finding is interesting as it shows that both of the peripheral clock genes tested (REV-ERBα and PPARα) behave differently following a course of treatment. Taken together the core clock genes as well as the peripheral clock genes tested could potentially be used as a 'panel' of biomarkers to determine disease status and whether the treatment for CML has been successful or not.

Figure 5:
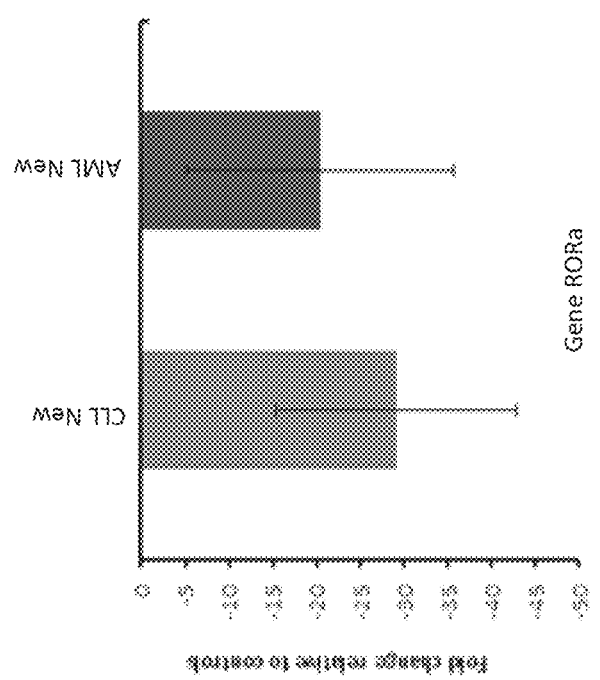
FIG. 5 is an exemplary graph of fold change in RORα gene expression in new cases of CLL and AML.

Changes in the gene expression of the peripheral clock gene RORα upon diagnosis in patients with either CLL or AML:

FIG. 5 depicts the changes in expression in the peripheral clock gene RORα peripheral clock gene expression in CLL and AML patients upon disease diagnosis. Gene expression was performed by qPCR using the ΔΔCt method using control samples as calibrant. Data was expressed as a fold change in ΔΔCt relative to the control samples which were given a value of 1.

RORα showed a very large down-regulation in expression in both CLL and AML patients upon diagnosis of both forms of leukemia compared to healthy control donors. In comparison to the other peripheral clock genes tested, this gene showed the greatest magnitude in down-regulation in AML patients upon disease diagnosis. The results suggest the possibility of RORa being used as a clinical biomarker for the diagnosis of both CLL and AML.

Figure 6:
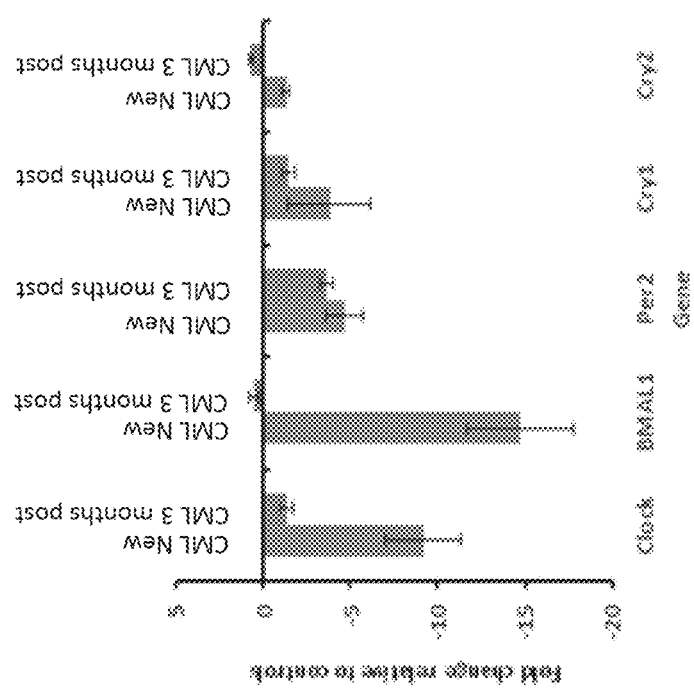
FIG. 6 is an exemplary graph of fold change in core clock gene expression in new cases of CML and cases of CML at the end of 3 months of treatment.
Figure 7A:
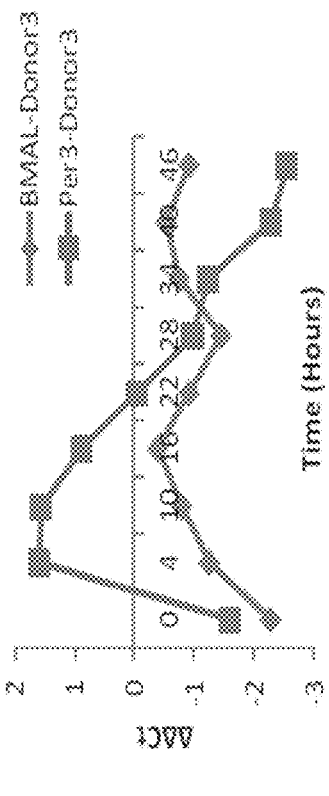
FIG. 7A is an exemplary graph of oscillatory patterns of BMAL1 and Per3 in Donor 1 sample after an attempt to synchronize the patterns in 10% FBS.
Figure 7B:
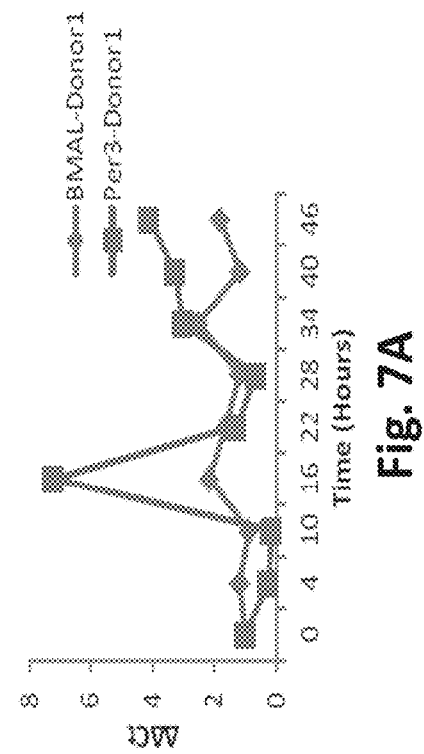
FIG. 7B is an exemplary graph of oscillatory patterns of BMAL1 and Per3 in Donor 2 sample after an attempt to synchronize the patterns in 10% FBS.
Figure 7C:
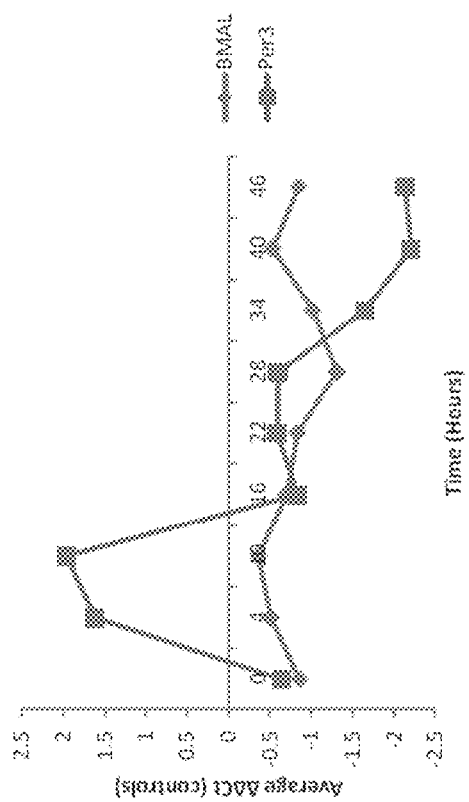
FIG. 7C is an exemplary graph of oscillatory patterns of BMAL1 and Per3 in Donor 3 sample after an attempt to synchronize the patterns in 10% FBS.
Figure 7D:
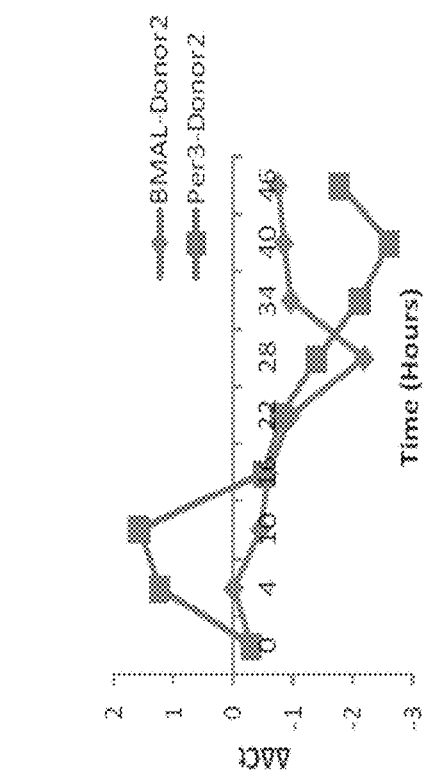
FIG. 7D is an exemplary graph of oscillatory patterns of BMAL1 and Per3 in an average of Donor 1, Donor 2 and Donor 3 samples after an attempt to synchronize the patterns in 10% FBS.
Figure 8A:
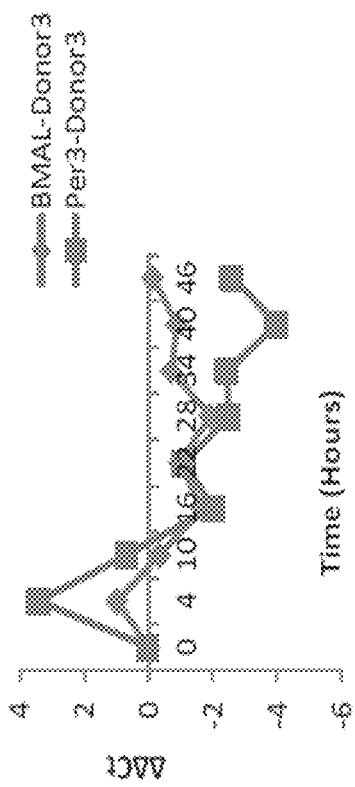
FIG. 8A is an exemplary graph of oscillatory patterns of BMAL1 and Per3 in Donor 1 sample after an attempt to synchronize the patterns in 50% FBS.
Figure 8B:
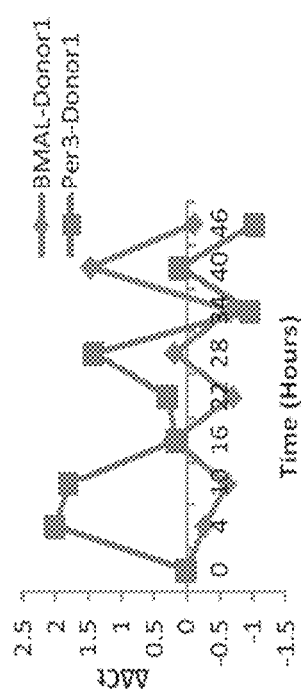
FIG. 8B is an exemplary graph of oscillatory patterns of BMAL1 and Per3 in Donor 2 sample after an attempt to synchronize the patterns in 50% FBS.
Figure 8C:
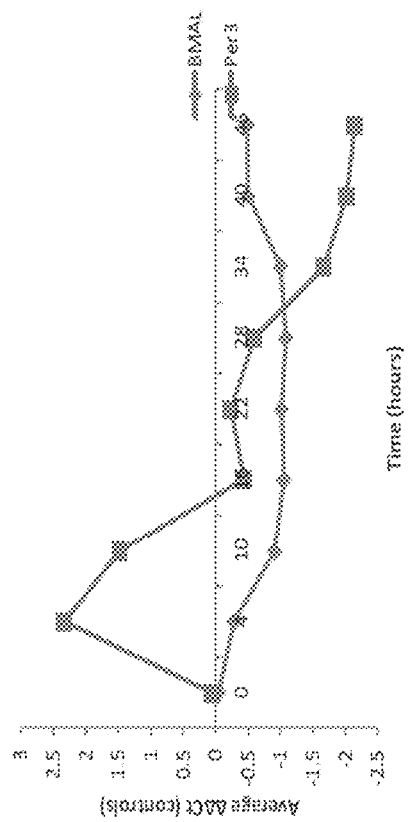
FIG. 8C is an exemplary graph of oscillatory patterns of BMAL1 and Per3 in Donor 3 sample after an attempt to synchronize the patterns in 50% FBS.
Figure 8D:
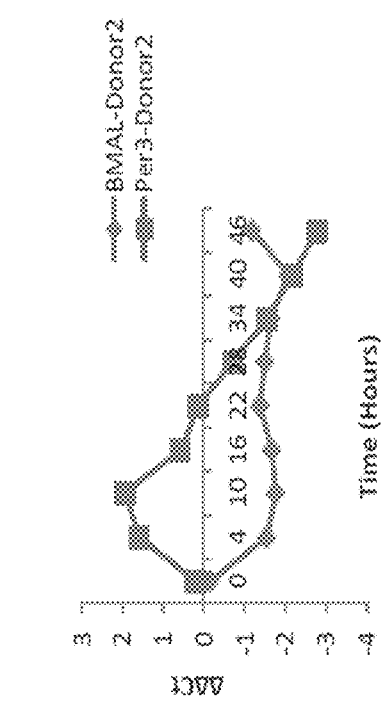
FIG. 8D is an exemplary graph of oscillatory patterns of BMAL1 and Per3 in an average of Donor 1, Donor 2 and Donor 3 samples after an attempt to synchronize the patterns in 50% FBS.

Changes in core clock gene expression in CML patients upon disease diagnosis and at the conclusion of treatment:

FIG. 6 depicts the changes in core clock gene expression in CIVIL patients at the point of disease diagnosis, and three months post-treatment. Gene expression was performed by qPCR using the ΔΔCt method using control samples as calibrant. Data was expressed as a fold change in ΔΔCt relative to the control samples which were given a value of 1.

The five core clock genes (CLOCK, BMAL1, PER2, CRY1 and CRY2) analyzed showed differences in expression between initial diagnosis for CML and following the standard three month course of chemotherapy treatment offered in Saudi Arabia. CLOCK, PER2 and CRY1 showed reduced down-regulation in expression after treatment relative to control samples from healthy donors. However, BMAL1 and CRY2 showed a complete reversal in gene expression and were found to be up-regulated relative to control samples after a course of treatment. These findings open up the possibility of these genes being used as clinical biomarkers in CML patients to determine disease status and treatment efficacy.

Temperature change is a synchronization method to assess clock gene oscillation In PBMC's:

The oscillation of the clock genes are important as this indicates the proper functioning of the biological clock. In the oscillation a subset of genes become activated and their expression increases during the day such as, BMAL1 and CLOCK while the expression of other genes such as Per2, Per3, Cry1 and Cry2 may be repressed during the day and activated during the night.

The genes that modulate the biological clock are divided into two types: the "core genes", such as Bmal, Clock, Per2, Per 3, Cry1 and Cry2, while the others form part of the peripheral clock such as Reverbα and RORα. Peripheral clock genes will only show oscillation if the core are also oscillating.

To measure the oscillation of the clock genes, the PBMC's were cultured as described in the materials and methods and then samples of the cells were taken every 6 hours from which RNA was extracted and used to measure the expression of the core clock genes.

In order to define the oscillation in core clock gene expression, PBMC's were first synchronised. In this regard three different conditions for cell synchronization were tested. Two of these conditions involved culturing the cells in the presence of either 10% FBS or 50% FBS for 1 hour, followed by two washes using fresh media after which the cells were harvested every 6 hours for the purpose of quantifying gene expression by qPCR.

In parallel, the method of cell-synchronization using temperature change was tested. In the temperature change method, the cells were first cultured in a $CO_2$ incubator at 32° C. for 12 hours after which the temperature of the incubator was increased to 37° C. and the cells cultured for a further 12 hours. Following this the cells were harvested in the usual way every 6 hours for the purpose of quantifying gene expression by qPCR.

For the cell synchronization experiments, the expression of both BMAL1 and Per 3 were measured every 6 hours over 72 hours using PBMC's derived period from three different healthy donors. As shown below in FIG. 7A, FIG. 7B, FIG. 7C, and FIG. 7D, (10% FBS), FIG. 8A, FIG. 8B, FIG. 8C, and FIG. 8D (50% FBS) and FIG. 9A, FIG. 9B, FIG. 9C, and FIG. 9D (temperature change), the oscillation of the both BMAL1 and Per3 is more apparent in cells that were synchronized using either the 50% FBS and temperature change methods compared to 10% FBS.

The synchronization of PBMC's using the temperature change method produced much better oscillation patterns compared to the 50% FBS method and the 10% FBS method, which did not yield any obvious oscillation patterns in BMAL1 and Per3 expression.

In future studies of PBMC's and core clock genes investigators may use the temperature change method as a means to synchronize the cells. This may also enable commercial companies to manufacture culture incubators that incorporate this temperature change method for the purposes of synchronising cell populations.

The oscillation of clock genes is dysregulated in Leukemic patients:

To assess the oscillation of clock genes in leukaemia patients, PBMC's were isolated from blood derived from patients newly diagnosed with AML. The cells were then synchronized using the temperature change method described above and cells were harvested every 6 hours over a 72 h time period.

From harvested cell samples, total RNA was isolated, reverse-transcribed into cDNA used in the qPCR assay to measure the expression levels of BMAL1 and Per 2.

Figure 10A:
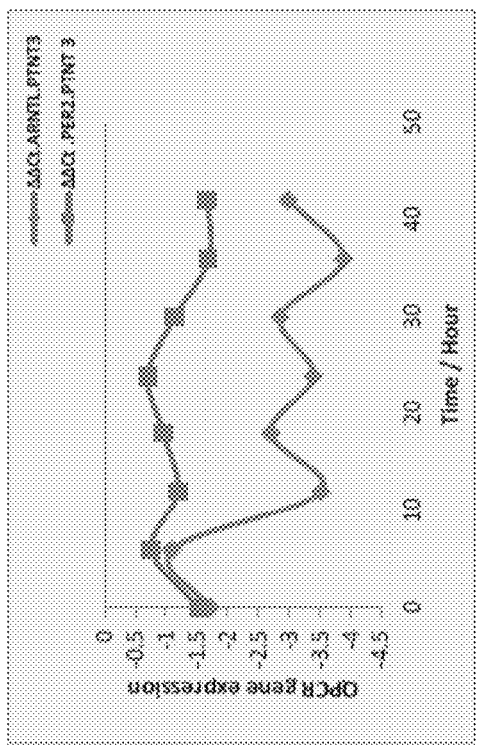
FIG. 10A is an exemplary graph of the loss of oscillation of BMAL1 and Per 2 in AML patients compared to healthy controls for patient 3.
Figure 10B:
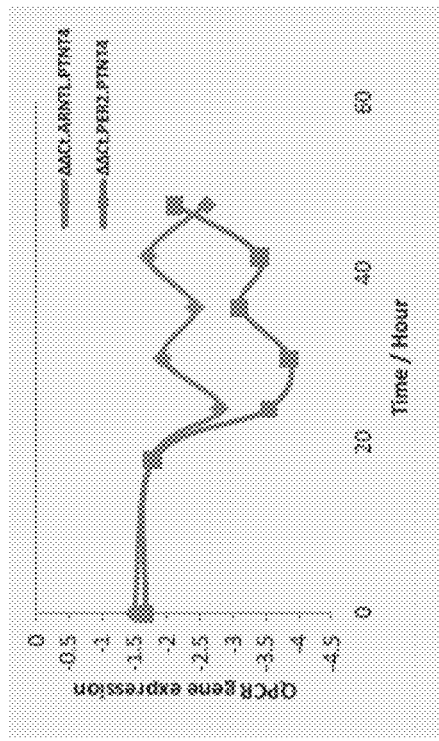
FIG. 10B is an exemplary graph of the loss of oscillation of BMAL1 and Per 2 in AML patients compared to healthy controls for patient 4.

As shown in FIG. 10A and FIG. 10B, the oscillation of BMAL1 and Per 2 is lost in AML patients compared to healthy controls. In total, 4 patients were tested, 2 did not show any oscillation (not shown) and 2 showed very marginal oscillation (FIG. 10A, Patient 3, and FIG. 10B, Patient 4). The observed results suggest that the oscillation of BMAL1 and Per2 is at the very least dysregulated if not completely lost in AML patients.

The oscillation of clock genes is lost in AML patients and could form the basis of a biomarker to assess both the severity and/or manifestation of AML.

The activation of the MAP Kinase pathway, p38, shows oscillations in AML patients and can be a potential target for treatment:

The kinase family of proteins represent one of the most important target classes for the treatment of leukemia. Members of this family include BCR-ABL, FLT3, PIM1 & 2 as well as a host of other MAP kinases. Whether the activation of these kinases show oscillations over time in samples derived from leukemia patients may be assessed.

The best conditions were assessed to activate the p38 pathway in PBMCs derived from AML patients. Cells were cultured in the presence of either 2% or 10% FBS followed by stimulation by either 20% FBS, 0.3 M Sorbitol or 1 mM Hydrogen peroxide ($H_2O_2$) for 30 minutes. Following the period of stimulation, cell lysates were prepared and used to assess phospho-p38 expression by western blot.

Figure 11:
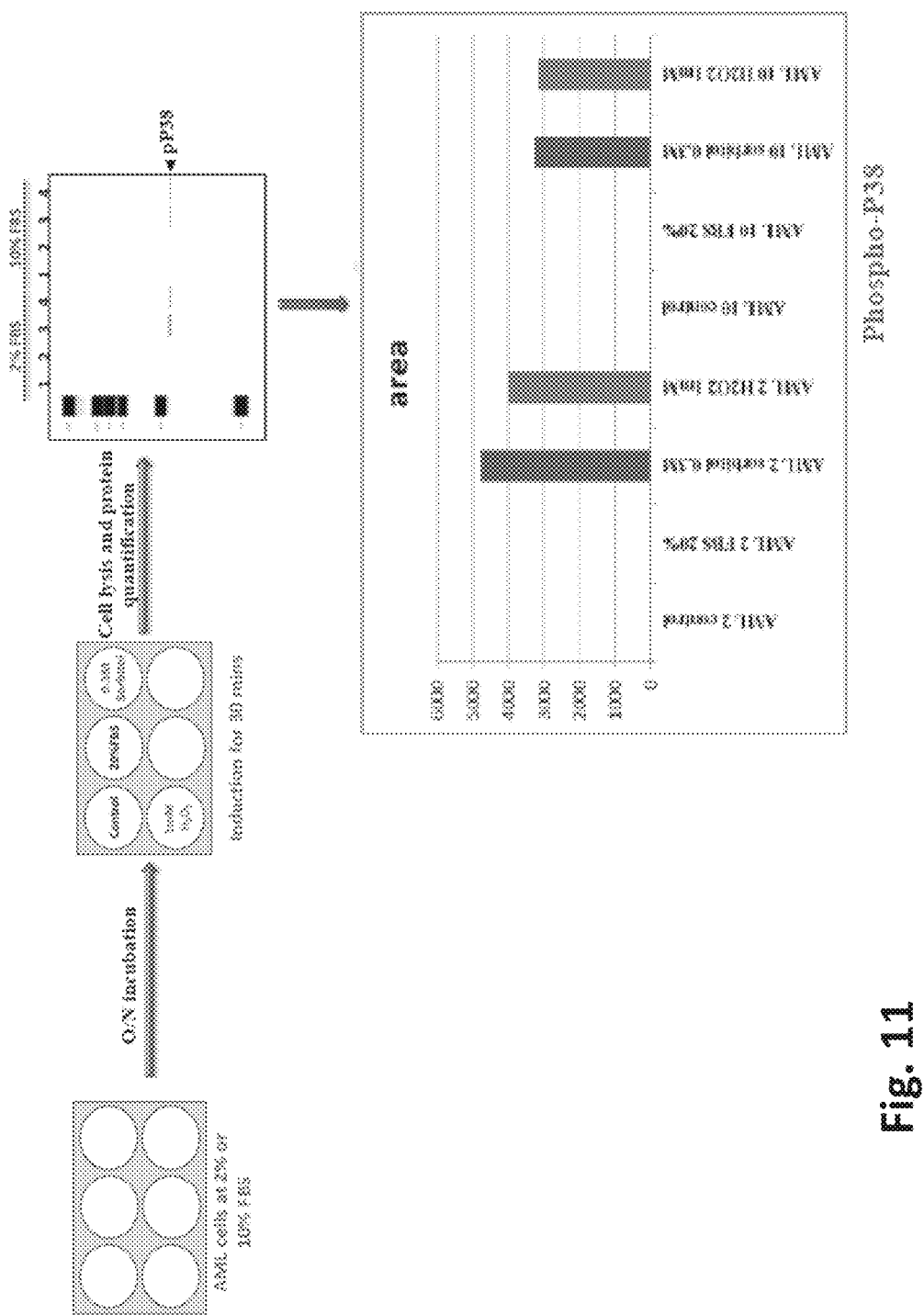
FIG. 11 is a diagram of the process employed to stimulate AML-PBMCs with 0.3 M sorbitol and 1 mM $H_2O_2$ cultured in 2% to observe the p38 protein phosphorylation.

As shown in FIG. 11, the stimulation of AML-PBMCs with 0.3 M sorbitol and 1 mM $H_2O_2$ cultured in 2% FBS was greater compared to cells cultured in 10% FBS. In addition, the stimulation with 10% FBS did not result in phosphorylation of p38.

In the next experiment the phosphorylation of p38 was induced over a period of 72 hours using 0.3 M sorbitol and lysates prepared every 6 hours over the time course. Lysates were then used to probe the phosphorylation of p38 by western blot and measured using the simple Western system (Protein simple).

Figure 12:
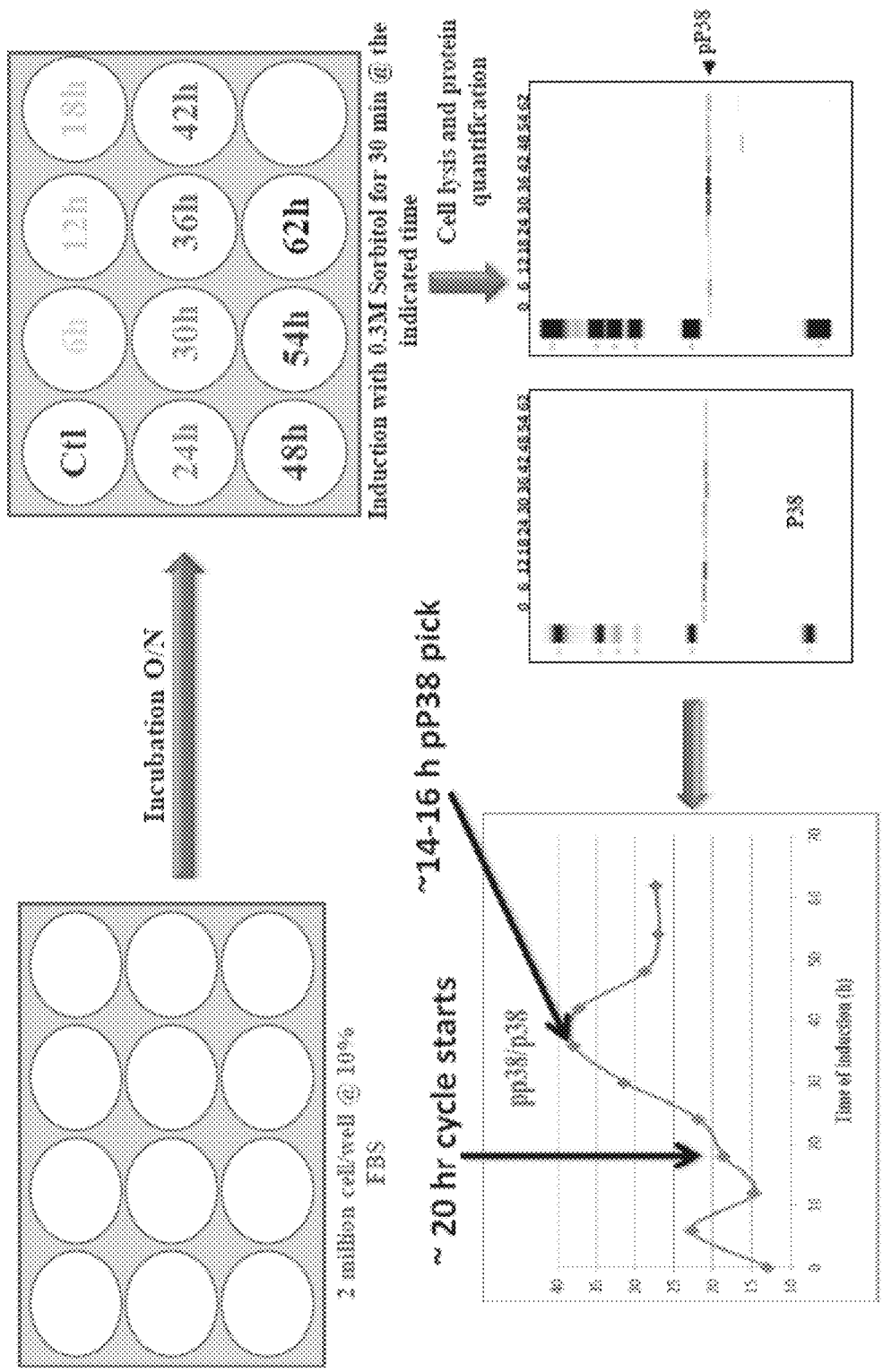
FIG. 12 is a diagram of the process employed to stimulate p38 phosphorylation pathways to observe oscillation of p38 phosphorylation.

As shown in the FIG. 12, the level of phosphorylation of p38 showed oscillation in the first 10 hours which then reached a maximum at around 40 hours following induction in culture. This corresponds to 14-16 hr for the clock cycle if we consider that the cycle starts after 20 hrs as shown in the FIG. 8. The phosphorylation of p38 shows oscillations and therefore the pathway regulating p38 phosphorylation also shows oscillations. The significance of this finding is that if phosphorylation of p38 is used as a target for treatment in leukemia, then drugs that target this would need to be given at specific times given that this pathway is not constitutively activated. This also raises the possibility of other members of the MAPK pathway such as BCR-ABL showing similar patterns of oscillation.

The invention claimed is:

1. A method for treating a human patient who has undergone a first treatment for chronic myeloid leukemia (CML) comprising:
   (A) continuing a first treatment with at least one of imatinib (Gleevec), dasatinib (Sprycel), nilotinib (Tasigna), bosutinib (Bosulif), ponatinib (Iclusig), Busulfan, Cyclophosphamide, or Cytarabine when:
   (i) the gene expression level of a human BMAL1 gene in plasma or peripheral blood mononuclear cells ("PBMC") taken from the human patient at a second time point relative to a first time point is increased by 1-fold to 18-fold;
   (ii) the gene expression level of human RORα and PPARα genes at the second time point relative to the first time point is increased by 1-fold to 3-fold; and
   (iii) the gene expression level of the human REV-ERBα gene at the second time point relative to the first time point is decreased by 2-fold to 5-fold; and
   administering to the human patient at least one of imatinib (Gleevec), dasatinib (Sprycel), nilotinib (Tasigna), bosutinib (Bosulif), ponatinib (Iclusig), Busulfan, Cyclophosphamide, or Cytarabine; and
   (B) discontinuing a first treatment with at least one of imatinib (Gleevec), dasatinib (Sprycel), nilotinib (Tasigna), bosutinib (Bosulif), ponatinib (Iclusig), Busulfan, Cyclophosphamide, or Cytarabine, and administering a second treatment that is different from the first treatment when:
(i) the gene expression level of the BMAL1 gene at the second time point relative to the first time point is decreased by 1-fold to 110-fold;
(ii) the gene expression level of RORα and PPARα genes at the second time point relative to the first time point is decreased by 5-fold to 40-fold; and
(iii) the gene expression level of the REV-ERBα gene at the second time point relative to the first time point is increased by 1-fold to 5-fold; and
administering at least one of imatinib (Gleevec), dasatinib (Sprycel), nilotinib (Tasigna), bosutinib (Bosulif), ponatinib (Iclusig), Busulfan, Cyclophosphamide, or Cytarabine as the second treatment, wherein the second treatment is different than the first treatment.

2. The method of claim 1 that comprises:
(A) continuing the first treatment when:
(i) the gene expression level of the human BMAL1 gene in peripheral blood mononuclear cells ("PBMC") taken from the human patient at a second time point relative to a first time point is increased by 1-fold to 18-fold;
(ii) the gene expression level of human RORα and PPARα genes at the second time point relative to the first time point is increased by 1-fold to 3-fold; and
(iii) the gene expression level of the human REV-ERBα gene at the second time point relative to the first time point is decreased by 2-fold to 5-fold; and
administering to the human patient at least one of imatinib (Gleevec), dasatinib (Sprycel), nilotinib (Tasigna), bosutinib (Bosulif), ponatinib (Iclusig), Busulfan, Cyclophosphamide, or Cytarabine.

3. The method of claim 1 that comprises:
(B) discontinuing the first treatment when:
the gene expression level of the BMAL1 gene at the second time point relative to the first time point is decreased by 1-fold to 110-fold;
the gene expression level of RORα and PPARα genes at the second time point relative to the first time point is decreased by 5-fold to 40-fold; and
the gene expression level of the REV-ERBα gene at the second time point relative to the first time point is increased by 1-fold to 5-fold; and
administering at least one of imatinib (Gleevec), dasatinib (Sprycel), nilotinib (Tasigna), bosutinib (Bosulif), ponatinib (Iclusig), Busulfan, Cyclophosphamide, or Cytarabine as the second treatment that is different than the first treatment.

4. The method of claim 1, wherein the second time point is 1 to 12 months after the first time point.

5. The method of claim 1 that further comprises determining the gene expression level of a CLOCK gene.

6. The method of claim 1 that further comprises determining the gene expression level of a CRY1 gene.

7. The method of claim 1 that further comprises determining the gene expression level of a CRY2 gene.

8. The method of claim 1 that further comprises determining the gene expression level of a PER2 gene.

9. The method of claim 1 that further comprises determining the gene expression level of a PER3 gene.

10. The method of claim 1 that further comprises determining the gene expression levels of CLOCK, CRY1, CRY2, PER2 and PER3 genes.

11. The method of claim 5, wherein gene expression of the CLOCK gene is increased between the first and second time points, and the first treatment is continued.

12. The method of claim 1, wherein gene expression of the REV-ERBα gene is decreased and expression of each of the PPARα and RORα genes is increased between the first and second time points, and the first treatment is continued.

13. The method of claim 1, further comprising determining the gene expression levels of CLOCK, PER2, CRY1, and CRY2 genes, and continuing the first treatment when expression of CLOCK, PER2 and CRY1 is increased between the first and second time points relative to control samples from healthy donors; and when expression of BMAL1 and CRY2 is increased between the first and second time points relative to control samples from healthy donors.

* * * * *